United States Patent
Begemann et al.

(10) Patent No.: US 8,690,761 B2
(45) Date of Patent: Apr. 8, 2014

(54) MINIMAL INVASIVE NEUROSURGERY ASSEMBLY AS WELL AS A METHOD FOR NEUROSURGERY USING SUCH A NEUROSURGERY ASSEMBLY

(75) Inventors: Malcolm Jon Simon Begemann, Velp (NL); Joachim Andreas Grotenhuis, Arnhem (NL); Wimold Pieter Steven Peters, Groningen (NL); Libbe Jitze Jonkman, Drachten (NL)

(73) Assignee: Neurendo B.V., Groningen (NL)

( * ) Notice: Subject to any disclaimer, the term of this patent is extended or adjusted under 35 U.S.C. 154(b) by 1059 days.

(21) Appl. No.: 12/574,519

(22) Filed: Oct. 6, 2009

(65) Prior Publication Data
US 2010/0145142 A1    Jun. 10, 2010

Related U.S. Application Data

(60) Provisional application No. 61/103,486, filed on Oct. 7, 2008.

(30) Foreign Application Priority Data

Oct. 7, 2008 (EP) .................................... 08166043

(51) Int. Cl.
*A61B 1/012* (2006.01)
*A61B 1/00* (2006.01)
*A61B 17/00* (2006.01)
*A61B 1/018* (2006.01)

(52) U.S. Cl.
CPC . *A61B 1/00* (2013.01); *A61B 17/00* (2013.01); *A61B 1/018* (2013.01)
USPC ............ 600/114; 600/115; 600/116; 600/117

(58) Field of Classification Search
CPC ....................................................... A61B 1/12
USPC ............ 24/129; 128/748; 600/137, 207, 310, 600/114–117, 121, 125; 604/167.01; 606/130
See application file for complete search history.

(56) References Cited

U.S. PATENT DOCUMENTS 4,646,752 A * 3/1987 Swann et al. .................. 600/561
4,681,103 A * 7/1987 Boner et al. ...................... 606/1
(Continued)

FOREIGN PATENT DOCUMENTS

WO    WO9219146    * 11/1992    ............... A61B 1/00
WO    WO9817191    * 4/1998    ............. A61B 19/00

OTHER PUBLICATIONS

WO03090834A2, Eversull Christian Scott, Expandable Guide Sheath and Apparatus and Methods Using Such Sheaths, Nov. 6, 2003.*

(Continued)

*Primary Examiner* — Clayton E Laballe
*Assistant Examiner* — Kevin Butler
(74) *Attorney, Agent, or Firm* — Birch, Stewart, Kolasch & Birch, LLP

(57) ABSTRACT

A minimal invasive neurosurgery assembly including a flush assembly having flush assembly main part with a central passage extending through the main part from the distal end to the proximal end along a longitudinal axis, and having at least one tool insertion assembly. The tool insertion assembly may include a tool handling part that is detachably connectable to the flush assembly main part and that has at least one tool insertion channel that extends from the distal end to the proximal end of the tool handling part. The tool insertion assembly may also include an inner sheath that is connected to the tool handling part and has an inner sheath wall and at least one lumen extending parallel to the longitudinal axis and in which an associated one of the at least one tool insertion channel emanates. The inner sheath may be insertable through the central passage of the flush assembly main part.

30 Claims, 20 Drawing Sheets

(56) References Cited

U.S. PATENT DOCUMENTS

| | | | | |
|---|---|---|---|---|
| 4,901,402 A * | 2/1990 | Begemann | ................. | 24/129 D |
| 5,092,839 A * | 3/1992 | Kipperman | ................. | 606/194 |
| 5,315,985 A * | 5/1994 | Decarie et al. | ................. | 600/101 |
| 5,486,155 A * | 1/1996 | Muller et al. | ................. | 600/137 |
| 5,575,814 A * | 11/1996 | Giele et al. | ................. | 607/127 |
| 5,700,262 A * | 12/1997 | Acosta et al. | ................. | 606/48 |
| 5,935,122 A * | 8/1999 | Fourkas et al. | ................. | 604/523 |
| 5,967,970 A * | 10/1999 | Cowan et al. | ................. | 600/207 |
| 6,358,200 B1 * | 3/2002 | Grossi | ................. | 600/156 |
| 6,652,492 B1 * | 11/2003 | Bell et al. | ................. | 604/167.01 |
| 7,479,146 B2 * | 1/2009 | Malinowski | ................. | 606/130 |
| 2010/0145142 A1 * | 6/2010 | Begemann et al. | ................. | 600/104 |
| 2011/0295066 A1 * | 12/2011 | Fan | ................. | 600/114 |

OTHER PUBLICATIONS

WO98/17191, Bernays, Rene, Self Locking Holding Device With Single-Point Fixation, Apr. 30, 1998.*

* cited by examiner

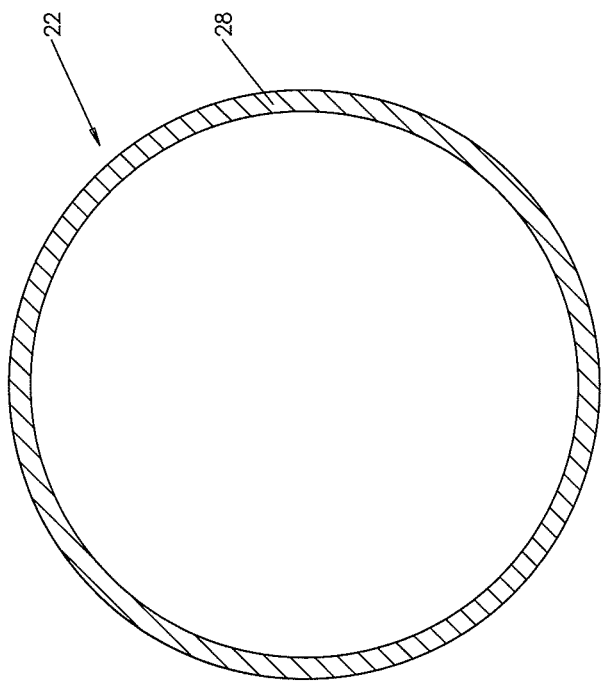
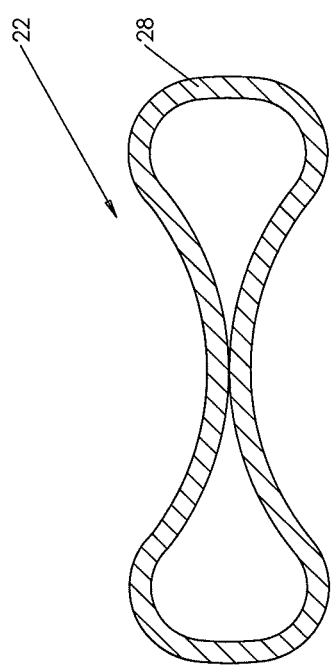
Fig. 19b
Fig. 19a

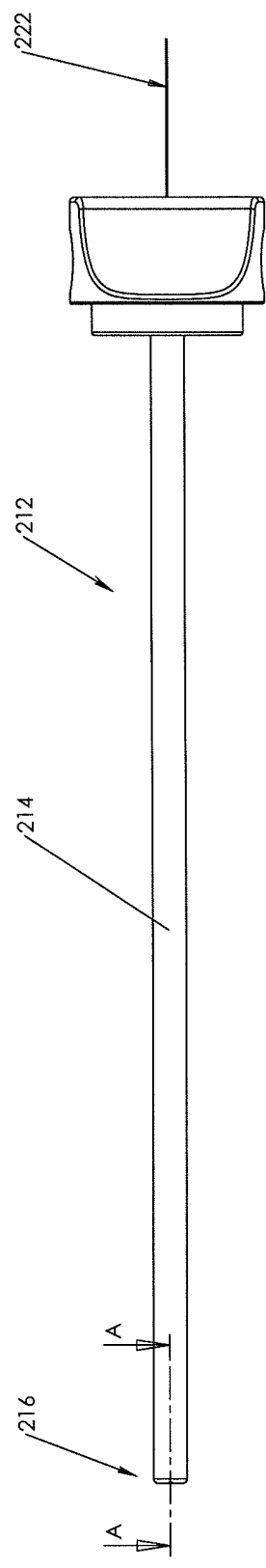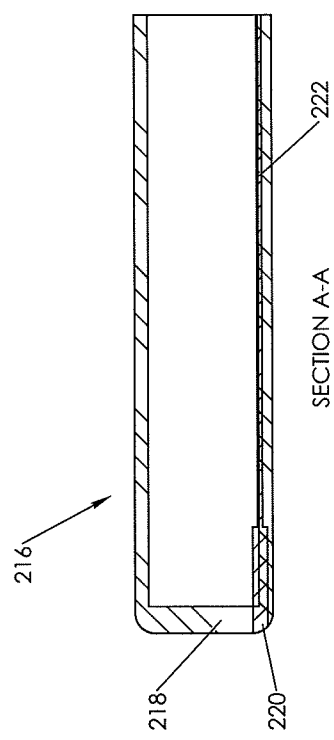
Fig. 23a
Fig. 23b
SECTION A-A

MINIMAL INVASIVE NEUROSURGERY ASSEMBLY AS WELL AS A METHOD FOR NEUROSURGERY USING SUCH A NEUROSURGERY ASSEMBLY

This Non-provisional application claims priority under 35 U.S.C. §119(e) on U.S. Provisional Application No(s). 61/103,486 filed on Oct. 7, 2008, and under 35 U.S.C. 119(a) to U.S. patent application Ser. No. 08166043.3 filed on Oct. 7, 2008 all of which are hereby expressly incorporated by reference into the present application.

TECHNICAL FIELD

The disclosure relates to a minimal invasive neurosurgery assembly, more particular, to a minimal invasive neurosurgery assembly that may be used for performing minimal invasive neurosurgery on the brain. The disclosure also relates to a method for performing minimal invasive neurosurgery using such an assembly.

BACKGROUND

Minimal invasive neurosurgery assemblies may, for example, be used for relieving fluid pressure from a brain cavity, for visual inspection of a brain with an endoscope, for taking a biopsy or for operating on brain tissue, e.g. the removal of a tumor.

In most cases, the known minimal invasive neurosurgery assemblies include an endoscope. When performing the operation, first it is established at which region of the brain action as to be taken. Subsequently, a location on the skull may be determined for drilling a hole in the skull. Next, the endoscope may be introduced via a hole in the skull into the brain tissue. Tools may be introduced via lumen that may be present in the endoscope.

A disadvantage of the known assemblies is that the tools that may be used with an endoscope, normally, have to be from the same brand as the endoscope. The dimensions are in most cases specific for a certain brand and interchanging tools between brands is not feasible. However, surgeons may prefer a tool of a first brand and an endoscope of another brand. In most cases, using such combinations is not feasible.

Another disadvantage is that it may be difficult and cumbersome to sterilize the endoscope and the tools after use, especially because the endoscope includes lumen for flushing and guiding tools. Sterilization and cleaning of lumen is notoriously difficult.

Yet another disadvantage is that when the view inside the brain has to be changed, the endoscope has to be move axially or be rotated along its longitudinal axis. This causes relative movement between parts of the endoscope and the brain tissue that is in direct contact with the endoscope. Such relative movement may cause damage to the brain tissue.

Another aspect of the known neurosurgery assemblies is that the endoscope has to be kept in the hands of the surgeon during the operation, thus leaving only one hand for controlling a tool. The endoscope may also be connected to tubes for supplying and discharging flushing fluid. These tubes may obstruct or impede the freedom of movement of the endoscope.

The present disclosure is directed, at least in part, to improving or overcoming some aspects of known neurosurgery assemblies.

SUMMARY OF THE INVENTION

In one aspect a minimal invasive neurosurgery assembly may be provided that may include:

a flush assembly having flush assembly main part with a distal end and a proximal end and with a central passage extending through the main part from the distal end to the proximal end along a longitudinal axis;

at least one tool insertion assembly including:

a tool handling part detachably connectable to the flush assembly main part, the tool handling part having a distal end and a proximal end and at least one tool insertion channel that extends from the distal end to the proximal end of the tool handling part; and an inner sheath connected to the tool handling part, the inner sheath having an inner sheath wall and at least one lumen extending parallel to the longitudinal axis and in which an associated one of the at least one tool insertion channel emanates, the inner sheath being insertable through the central passage of the flush assembly main part.

In another aspect a method for performing neurosurgery operation on the brain is provided. The method includes:

providing the neurosurgery assembly as described hereabove;

determining a region in which the operation has to be performed and based on that determining a position at which a hole has to be drilled in the skull;

drilling a hole in the skull;

inserting an inner sheath of the assembly through the hole;

inserting at least one of an endoscope and a tool into the tool insertion assembly through an associated tool insertion channel into an associated one of the lumen of the inner sheath.

After determining in which region the operation has to be performed and at which position a hole has to be drilled in the skull, the hole may be drilled in the skull. Subsequently, the inner sheath of the tool insertion assembly may be inserted through the hole in the skull. Before or after insertion of the inner sheath, an endoscope may be inserted into the tool insertion assembly, more particularly through a tool insertion channel into one of the lumen of the inner sheath. Tools may be inserted into the tool insertion assembly through a tool insertion channel into one of the lumen of the inner sheath.

An advantage of such an assembly and method is that the endoscope to be used therewith does not have to include flushing lumen. Consequently the notoriously difficult cleaning and sterilizing of the flushing lumen of the endoscope is not anymore necessary. The endoscope only has to be cleaned and sterilized at outer surfaces which is much easier and reduces the risk of infections.

Another advantage of such an assembly and method is that the tool insertion assembly may have lumen of which the diameter may be as desired by the surgeon. Consequently, the surgeon may operate with a endoscope of brand X and use tools of brand Y. This greatly enhances the flexibility of the use of tools.

Yet another advantage may be that the neurosurgery assembly may be of a single use type that may be disposed after the operation. Cleaning and sterilization of lumen is not necessary, which saves costs. In an embodiment, the inner sheath wall may have a first position and a second position. When the inner sheath wall is in the first position it may have, in cross section, an outer circumference that is convex. When the inner sheath wall is in the second position it may have, in cross section, an outer circumference that includes concave parts so that the total cross sectional area of the inner sheath having its wall in the second position is reduced relative to the total cross sectional area of the inner sheath having its wall in the first position. When the tool insertion assembly is inserted into the brain tissue, the inner sheath wall may be in the second position. Because of the reduced cross sectional area in the second stable position, damage to the brain tissue when inserting the tool insertion assembly may be minimized. In an embodiment both the first and the second position may be stable positions. However, in another embodiment it is also possible that only the second position is a stable position. In that embodiment, the first position may be obtained by inserting a tool into a lumen of the inner sheath.

In yet another embodiment the neurosurgery assembly may include an outer sheath with a distal end and a proximal end. The outer sheath may have an outer sheath wall that bounds an outer sheath channel that extends along a longitudinal axis and that has a distal opening at the distal end and an proximal opening at the proximal end. The flush assembly main part may be connected to the outer sheath adjacent the proximal end of the outer sheath and the outer sheath channel may be connected to the central passage, the inner sheath being insertable into outer sheath channel. A fixation assembly may be provided that is configured to connect the outer sheath with a skull of a patient. The fixation assembly may be placed in the hole in the skull and the outer sheath may be inserted through the hole and through the brain tissue so that a distal end of the outer sheath is at the desired region in the brain. It may also be feasible to first insert the outer sheath and subsequently place the fixation assembly in the hole in the skull. The fixation assembly may fixate the outer sheath relative to the skull. After fixation, which may, in an embodiment, be effected by exerting a clamping force on the outer sheath, the outer sheath does not have to be moved relative to the brain tissue any more. Neither axial movement nor rotation of the outer sheath that may be a stiff, tubular part, relative to the brain tissue is necessary. Thus the chance of damage of brain tissue during the operation may be reduced.

In an embodiment having an outer sheath, the outer sheath wall may have a first position and a second position. When the outer sheath wall is in the first position it may have, in cross section, an outer circumference that is convex. When the outer sheath wall in the second position it may have, in cross section, an outer circumference that includes concave parts so that the total cross sectional area of the outer sheath having its wall in the second position is reduced relative to the total cross sectional area of the outer sheath having its wall in the first position. Because of the reduced cross sectional area in the second position, damage to the brain tissue when inserting the tool insertion assembly may be minimized. In an embodiment both the first and the second position may be stable positions. However, in another embodiment it is also possible that only the second position is a stable position. In that embodiment, the first position may be obtained by inserting a tool insertion assembly into the outer sheath channel of the outer sheath.

As stated, the minimal invasive neurosurgery assembly may include a flush assembly with a flush assembly main part.

In an embodiment the tool insertion assembly may be rotatable relative to the flush assembly around the longitudinal axis. The flush assembly may be connected to tubes via which flushing fluid may be supplied and discharged. Because the flush assembly main part may be stationary during the operation, the tubes may be stationary as well even when the tool insertion assembly, the tools or an endoscope to be used with the neurosurgery assembly are rotated or axially moved. As the tool insertion assembly may be rotatable relative to the flush assembly, the freedom of movement of the tools may be enhanced because fluid supply and discharge tubes that may be connected to the flush assembly main part may remain stationary and thus do not obstruct or impede the freedom of movement for the surgeon.

In embodiments having an outer sheath, the flush assembly main part may be connected to the outer sheath adjacent the proximal end of the outer sheath and the outer sheath channel may be connected to the central passage.

As stated, the minimal invasive neurosurgery assembly may include at least one, but generally more than one, tool insertion assembly that may have a tool handling part that may be detachably connectable to flush assembly main part. The tool insertion assembly may be used as a guide for inserting tools. The tool insertion assembly may include an inner sheath with at least one lumen. A proximal end of the inner sheath may be connected with the tool handling part. When an endoscope having a diameter of, for example 2.2 mm has to be used, a tool insertion assembly may be used that has an inner sheath with a lumen that has such a diameter. However, when another endoscope is desired, for example with a diameter of 2.8 mm, a different tool insertion assembly may be used. The inner sheath generally will have more than one lumen so that also tools may be introduced into the inner sheath parallel to the endoscope. In the embodiments having an outer sheath, inner sheaths having lumen combinations of different diameters may be easily exchanged during the operation without the risk of damaging the brain tissue. Also endoscopes and tools may be easily exchanged without the risk of damaging brain tissue. In the embodiments having an outer sheath, also rotation of the inner sheath with an endoscope and/or tools inserted therein may be possible without the risk of damaging brain tissue. Because of the various diameter combinations of the lumen that may be provided in the inner sheath, it may also be possible to use the endoscope of brand X and simultaneously use the tools of brand Y. Thus the surgeon obtains an optimal flexibility in his choice of tools and endoscopes.

In an embodiment the neurosurgery assembly may include a connector to axially fixate the inner sheath relative to an endoscope that may be inserted into the at least one lumen of the inner sheath. In such an embodiment without an outer sheath, the surgeon may hold the inner sheath and by manipulating the inner sheath also steer the endoscope. Alternatively, the surgeon may hold the endoscope an by manipulating the endoscope also move the inner sheath. In an embodiment with an outer sheet, it may also be advantageous to have a connector that axially fixes the endoscope relative to the inner sheath, for example, when the surgeon has to manipulate two other tools that may be inserted through the tool insertion assembly.

The number of times that the tool insertion assembly has to be exchanged may be reduced with an embodiment of which the inner sheath may have at least one lumen of which the dimension may be changed by virtue of a flexible wall part of the lumen. The flexible wall part may, in one embodiment, have two stable positions so that the lumen may be fit for accommodating without play a tool having a first diameter when the at least one flexible wall part is in the first stable position, and for accommodating without substantial play a tool having a second diameter that is different from the first diameter when the at least one flexible wall part is in the second stable position. In another embodiment, the flexible wall part may have a single stable position to which it is biased. When a tool with a larger diameter is inserted, the flexible wall part may flex to accommodate the tool substantially without radial play.

The inner sheath may also include flush lumen for supplying and discharging flushing fluid to the relevant region in the brain. The flush assembly main part may include ring channels that connect via a flush passage in the wall of the inner sheath with the flush lumen for supplying and discharging flushing fluid. Thus the fluid connection between the tubes that may be connected to the generally stationary flush assembly main part and the flush lumen in the inner sheath may be maintained even during rotation of the inner sheath. Because the endoscope to be used with such an embodiment does not have to include flushing lumens and because, consequently, no flushing fluids have to flow through lumen in the endoscope, cleaning and sterilizing of the endoscope will be much easier as only the outside has to be sterilized. Additionally the diameter of the endoscope may be reduced relative to endoscopes having lumen for flushing fluid.

In one embodiment the tool handling part may include at least one tool insertion channel that emanates into a flush lumen. The tool insertion channel may include a valve. Normally, the valve will be in the closed position, so that flushing fluid will not flow in a proximal direction out of the neurosurgery assembly. The valve may open when a tool is inserted into the tool insertion channel and the flush lumen. Thus, the flush lumen may have a twofold function, namely: the function of a passage for flushing fluid and the function of a passage for a tool. In one embodiment it may be feasible that the cross section of the flush lumens is non-circular so that, even when a circular tool is inserted into the flush lumen, fluid may escape from the brain cavity. Additionally, provisions may be present, such as ridges or the like that prevent that a tool inserted in a flush lumen closes off a fluid passage that may form the fluid connection between the flush lumen and a ring channel. A similar valve may also be present in a tool insertion channel that emanates in a lumen for guiding tools. With those valves a more controlled draining of a brain cavity may be accomplished.

One of the tool insertion assemblies may have a dummy inner sheath that may be solid and that may be inserted in the outer sheath before the outer sheath is inserted into the brain tissue so as to close off the distal opening of the outer sheath. The dummy inner sheath may have a rounded distal tip to reduce brain tissue damage during insertion of the outer sheath into the brain tissue. In one embodiment the tip may be transparent and the dummy inner sheath may include a channel for accommodating an endoscope. With such an embodiment, the outer sheath with the dummy inner sheath inserted therein, may be inserted into the brain while looking through the endoscope so that the surgeon may view the region that is being penetrated by the neurosurgery assembly. In the embodiment with the transparent tip, the tip may be rounded as well. A flat part may be present in the transparent tip to improve the image that may be obtained with the endoscope that receives its image via the transparent distal tip.

In an embodiment a pressure sensor may be provided that may be configured to provide a signal that is indicative of one of fluid pressure and thrust force. The pressure sensor may, for example, be provided in the distal end of the dummy sheath and/or in the distal end of the inner sheath and/or in the flushing assembly main part. The pressure sensor may be used for measuring fluid pressure, for example body fluid pressure inside brain cavities and/or flushing fluid pressure during flushing. The pressure sensor may also be used for measuring thrust force that may be exerted on the distal end of the dummy inner sheath when inserting the neurosurgery assembly into the brain.

In an embodiment, the neurosurgery assembly may include a dummy tool that may be insertable into the at least one lumen of the inner sheath. The dummy tool may have at least one dummy tool insert of which at least a distal end is closed off. The length of the at least one dummy tool insert may be such that in a mounted condition of the dummy tool on the tool handling part, the distal end of the at least one dummy tool insert also closes off the distal opening of an associated one of the at least one lumen. By using such a dummy tool, the inner sheath may be inserted into the brain with reduced chance of brain damage.

In an embodiment, an insertion depth indicator may be provided that indicates a character that may be indicative for the insertion depth of the outer sheath or the inner sheath. The character may be a number. The insertion depth indicator may be provided on the fixation assembly. In the variant without the outer sheath, the insertion depth indicator may be provided on the flush assembly main part. The flush assembly main part may be an integral part of the fixation assembly. Alternatively, the flush assembly main part may be connectable to the fixation assembly. The insertion depth indicator may be configured to be visible from a proximal end of the neurosurgery assembly when looking in the direction of a distal end of the neurosurgery assembly. That provides the advantage that the surgeon does not have to move his head away from the endoscope when he wants to know to what extend the neurosurgery assembly has been inserted into the brain.

In an embodiment the parts of neurosurgery assembly, the outer sheath, the flush assembly, the tool insertion assembly, and the fixation assembly may be manufactured from rigid plastic and may be disposed of after a single use. Thus the cleaning and sterilization problem of lumens that are in direct contact with body fluids may be solved.

The disclosure also relates to a kit of parts including a single outer package that contains a neurosurgery assembly as described in a sterilized atmosphere. The kit may include a selection of different tool insertion assemblies so that the surgeon will have optimal flexibility during the operation.

Other aspects are described in the dependent claims and will be elucidated in the detailed description.

BRIEF DESCRIPTION OF THE DRAWINGS

FIG. 16b is a side elevation view of the embodiment of the fixation assembly shown in FIG. 16a;

FIG. 19a is a cross section of an embodiment of a collapsible outer sheath in a collapsed state;

FIG. 19b is a cross section of the embodiment of FIG. 19a in a non-collapsed state;

FIG. 23a is an elevation view of an embodiment of dummy tool insertion assembly that may be inserted in an outer sheath;

FIG. 23b is a cross section of the tip of the dummy tool insertion assembly of FIG. 23a.

DETAILED DESCRIPTION

Figure 1:
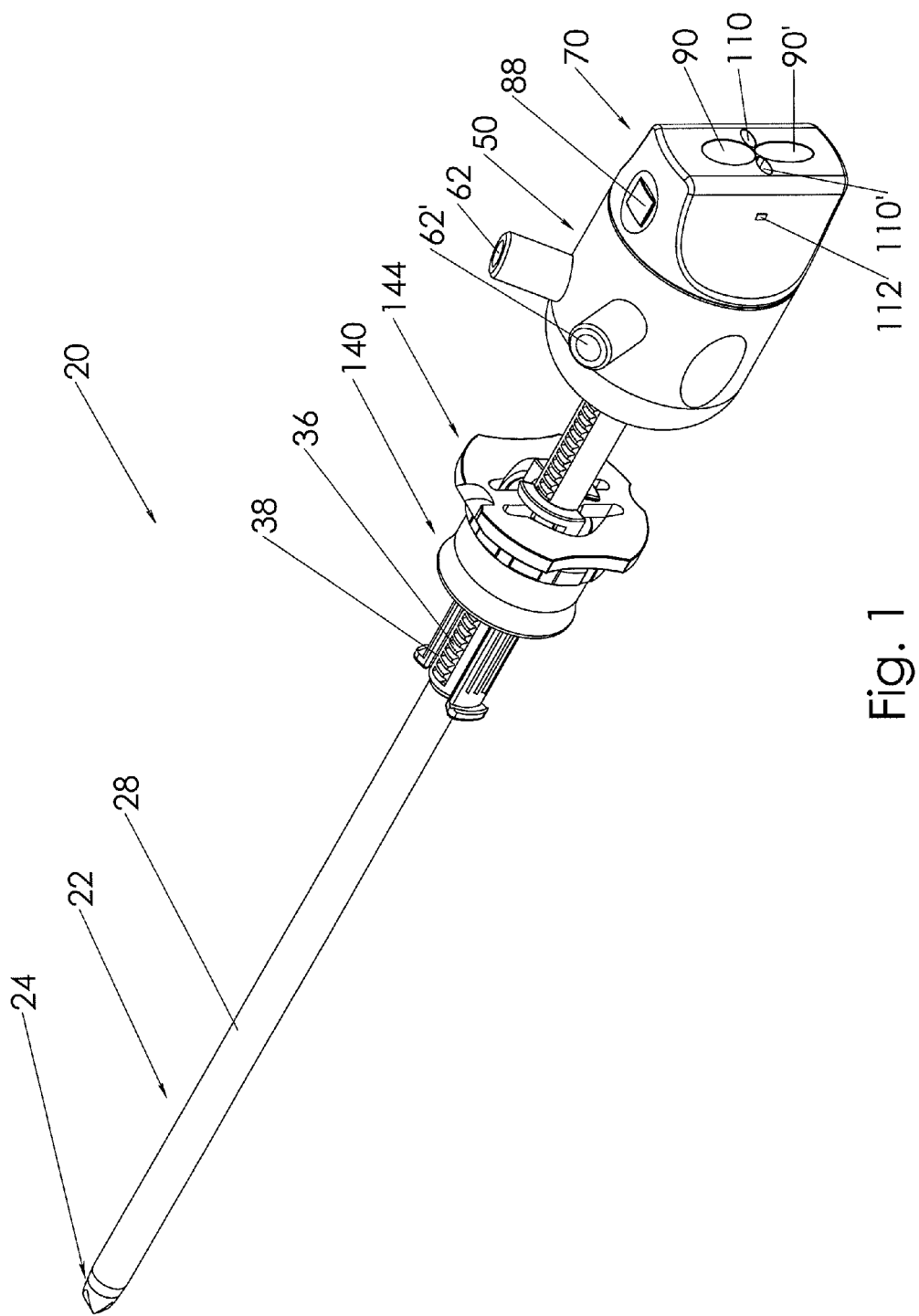
FIG. 1 is a perspective view of an embodiment.

The minimal invasive neurosurgery assembly 20 of which embodiments will be described may in one embodiment have a flush assembly 50 and a tool insertion assembly 70. Such an embodiment may include a fixation assembly 140, 180, 270 that may be configured to connect the inner sheath 96 with a skull S of a patient. An embodiment could, for example, look like the embodiment depicted in FIGS. 1-10, be it that the outer sheath 22 depicted therein may not be present in such an embodiment and that the flush assembly 50 may be connectable to the fixation assembly 140, 180.

Figure 2:
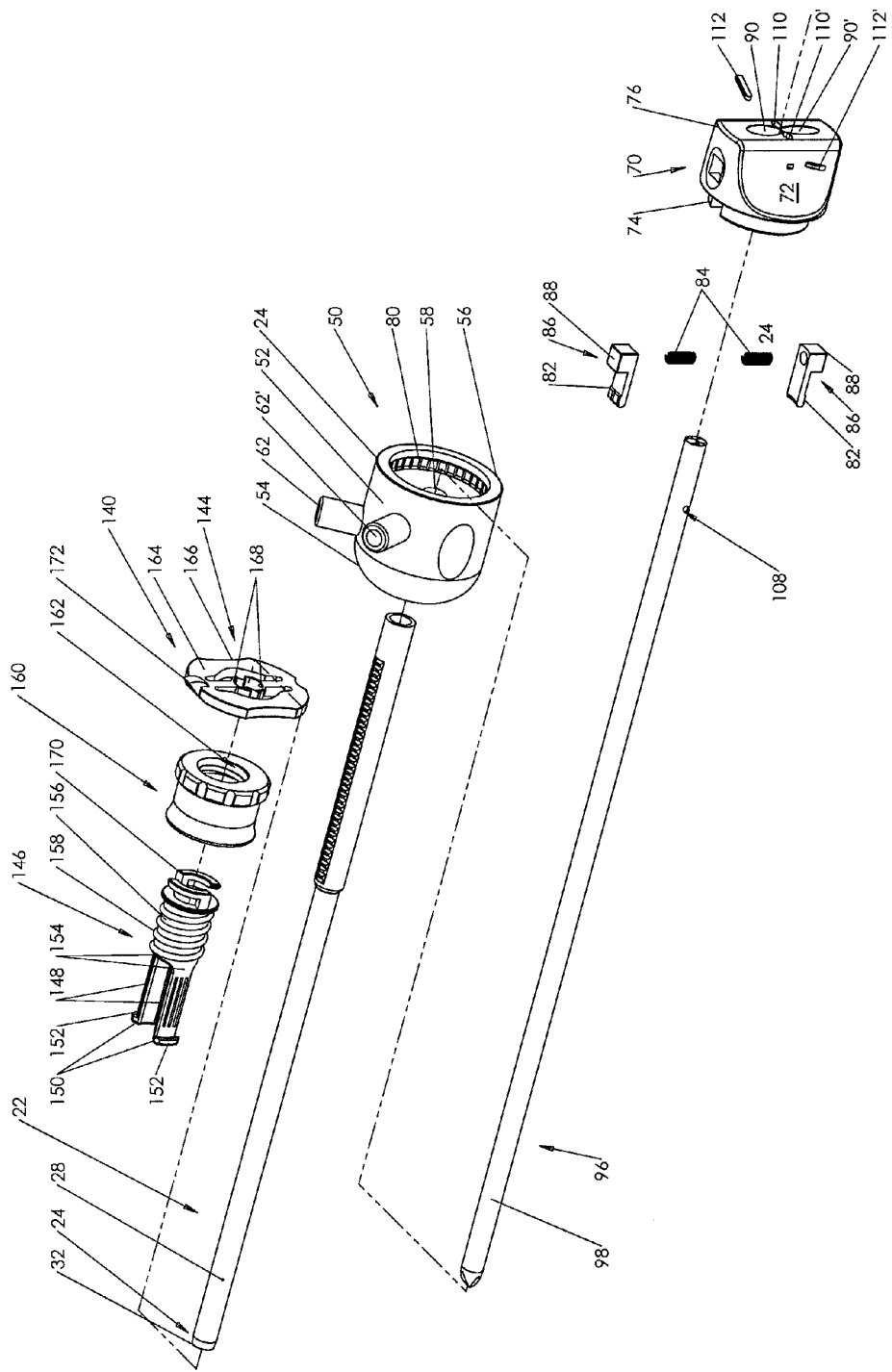
FIG. 2 is an exploded view of the embodiment shown in FIG. 1.
Figure 3:
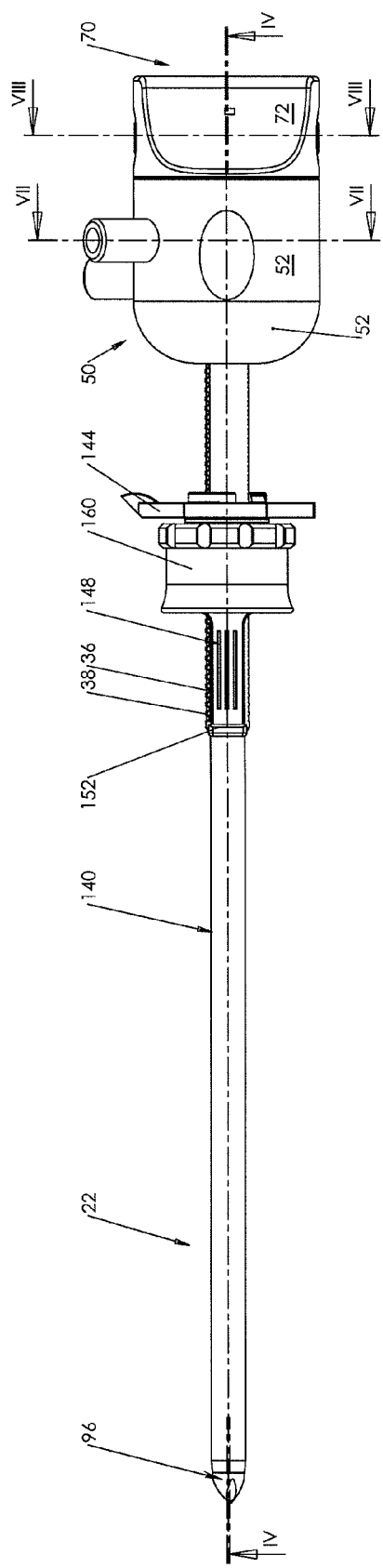
FIG. 3 is a side elevation view of the embodiment shown in FIG. 1.
Figure 4:
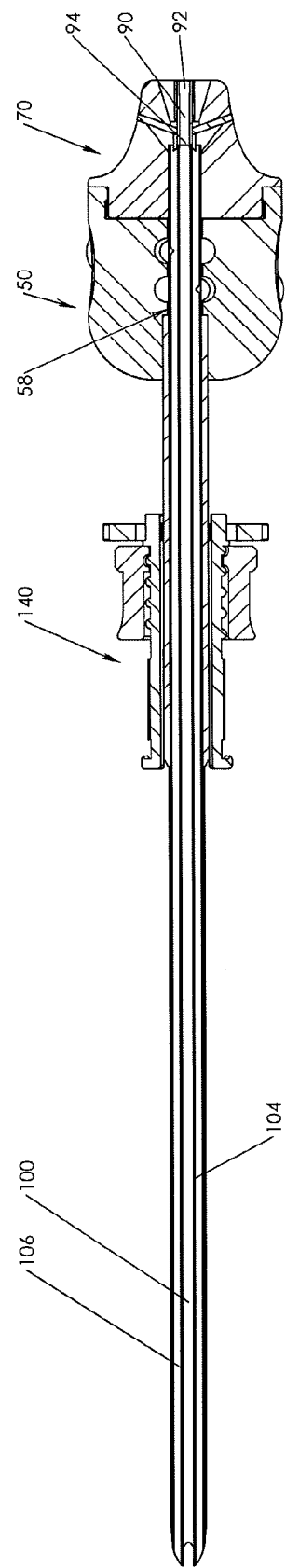
FIG. 4 is cross section over line IV-IV in FIG. 3.
Figure 5:
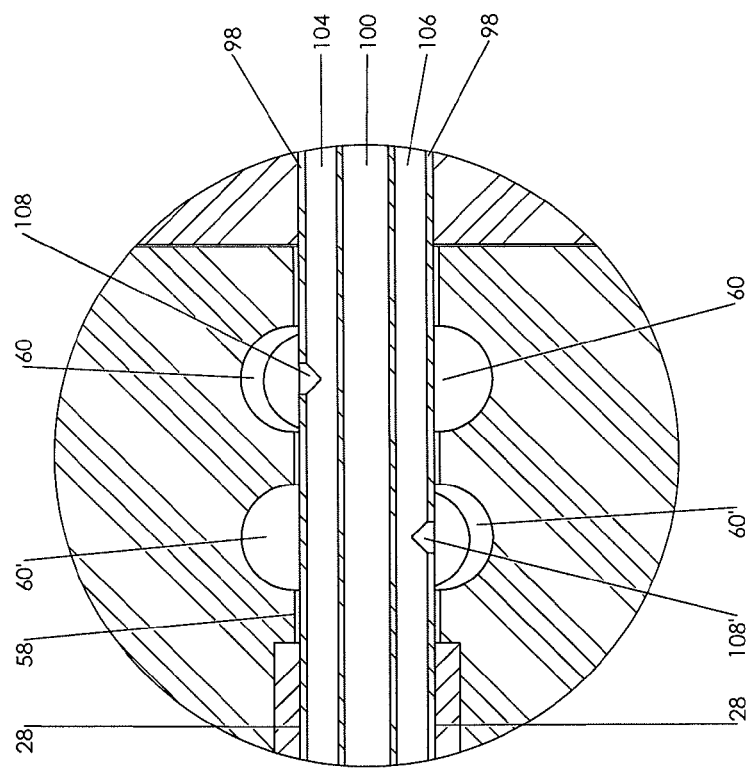
FIG. 5 is a detail of FIG. 4.
Figure 8:
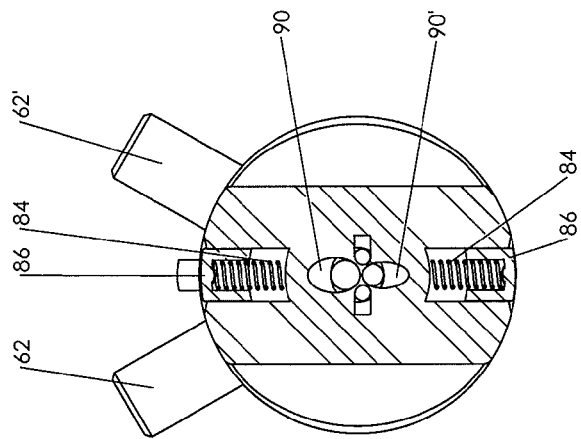
FIG. 8 is a cross section over line VIII-VIII in FIG. 3.
Figure 7:
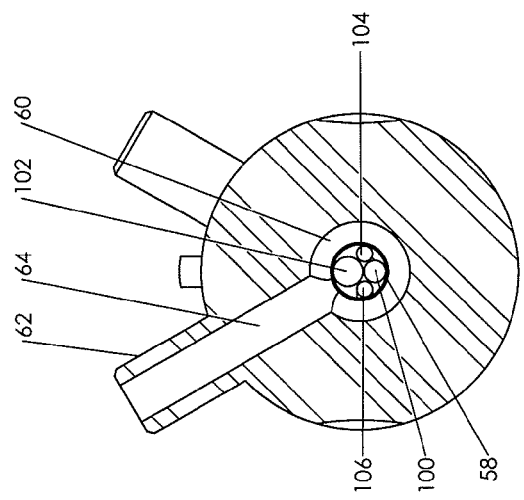
FIG. 7 is a cross section over line VII-VII in FIG. 3.
Figure 6:
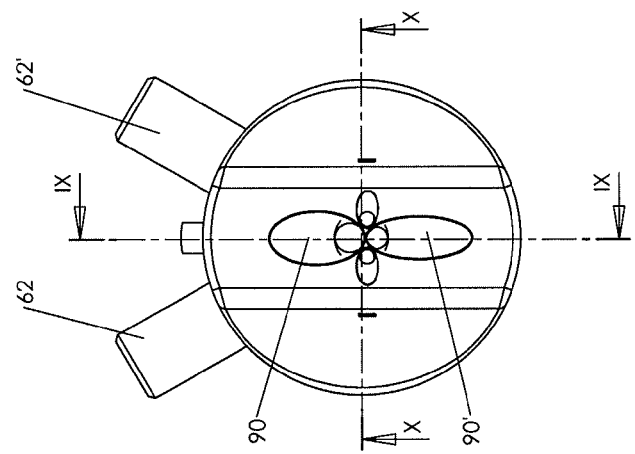
FIG. 6 is an elevation view from the right side of the embodiment in FIG. 3.
Figure 9:
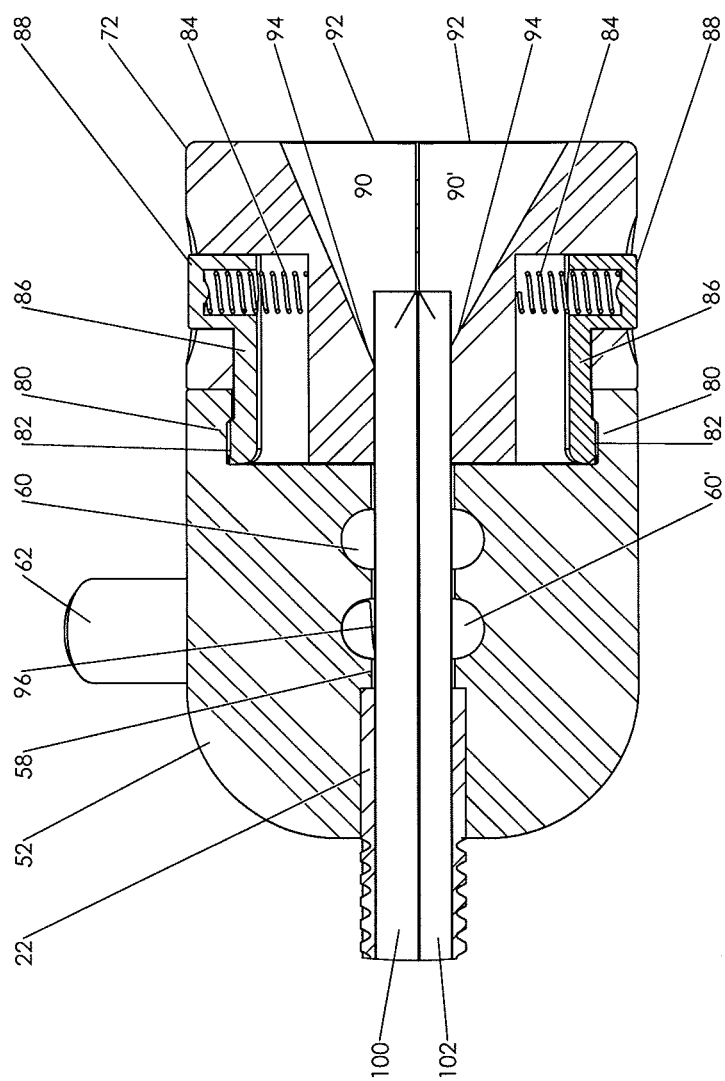
FIG. 9 is a cross section over line IX-IX in FIG. 6

An alternative embodiment may include an outer sheath 22. An example of such an embodiment is shown in FIGS. 1-10. Embodiments with an outer sheath 22 may also be provided with a fixation assembly 140, 180 that may be configured to connect the outer sheath 22 with a skull S of a patient. The outer sheath 22, of which an embodiment is shown in FIG. 2, may have a distal end 24 and a proximal end 26. The outer sheath 22 may have an outer sheath wall 28 that may bound an outer sheath channel 30 that extends along a longitudinal axis L and that has a distal opening 32 at the distal end 24 and an proximal opening 34 at the proximal end 26. The outer sheath may have a scale 38 on the outer sheath wall 28. The outer sheath may also have a structure on the outer sheath wall 28 that may be used for connecting the outer sheath to a fixation assembly. The structure may be embodied as ridges, notches, or, for example, a bayonet structure 36 as depicted. In FIG. 1, the raised parts of the bayonet structure 36 may include numbers to indicate the scale 38. These numbers or characters are not shown in FIG. 2 but it is indicated by reference number 38 where they may be applied. Of course, also other positions for applying the numbers of the scale 38 are feasible. The outer sheath 22 may be manufactured from rigid plastic material or from a metal. It may be manufactured by extrusion.

In an alternative embodiment of the outer sheath 22 the outer sheath wall 28 may have a first position and a second position. The outer sheath wall 28 may in the first position have, in cross section, an outer circumference that is convex. In the second position, the outer sheath wall 28 may have, in cross section, an outer circumference that includes concave parts so that the total cross sectional area of the outer sheath 22 having its wall 28 in the second position may be reduced relative to the total cross sectional area of the outer sheath 22 having its wall 28 in the first position. FIGS. 19a and 19b show an example of such an embodiment. FIG. 19a shows the second (collapsed) position and FIG. 19b shows the first (non-collapsed) position. Both the first and the second position may be stable positions. In an alternative embodiment only the second position may be a stable position. For that embodiment, the first position may be obtained by inserting an inner sheath 96 in the outer sheath 22.

The flush assembly 50, of which an embodiment is shown in FIGS. 1-9 may include flush assembly main part 52 with a distal end 54 and a proximal end 56 and with a central passage 58 extending through the main part 52 from the distal end 54 to the proximal end 56. In the embodiment with the outer sheath 22, the main part 52 may be connected to the outer sheath 22 adjacent the proximal end 26 of the outer sheath 22 and the outer sheath channel 30 may be connected to the central passage 58. In the embodiment without the outer sheath 22 the flush assembly main part 52 may be connected to or, alternatively connectible to a fixation assembly 140, 180, 270.

The tool insertion assembly 70 may include a tool handling part 72 that may be detachably connectable to flush assembly main part 52. The tool handling part 72 may having a distal end 74 and a proximal end 76. An inner sheath 96 may be connected to the tool handling part 72. The inner sheath 96 may have an inner sheath wall 98 and the inner sheath may have at least one lumen 100, 102, 104, 106 extending parallel to the longitudinal axis L. The inner sheath 96 may be insertable through the central passage 58 of the flush assembly main part 52. In the embodiments with an outer sheath 22, the inner sheath 96 will also extend into the outer sheath channel 30. An embodiment of an inner sheath 96 is shown in the exploded view of FIG. 2. As stated, normally the inner sheath 96 will be connected to the tool handling part 72. The inner sheath wall 98 may include at least one flush passage 108 that extends through the inner sheath wall 98. One such flush passage 108 is visible in FIG. 2. The inner sheath 96 may have all kinds of cross sections. Some examples are shown in FIGS. 18a, 18b, 18c and FIGS. 20, 21, 22 that will be discussed later.

Figure 18A:
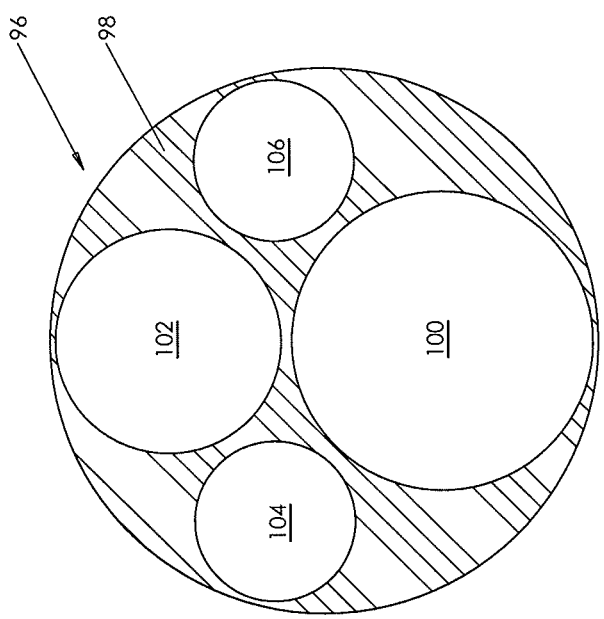
FIG. 18a is a cross-section of a first embodiment of an inner sheath.
Figure 18C:
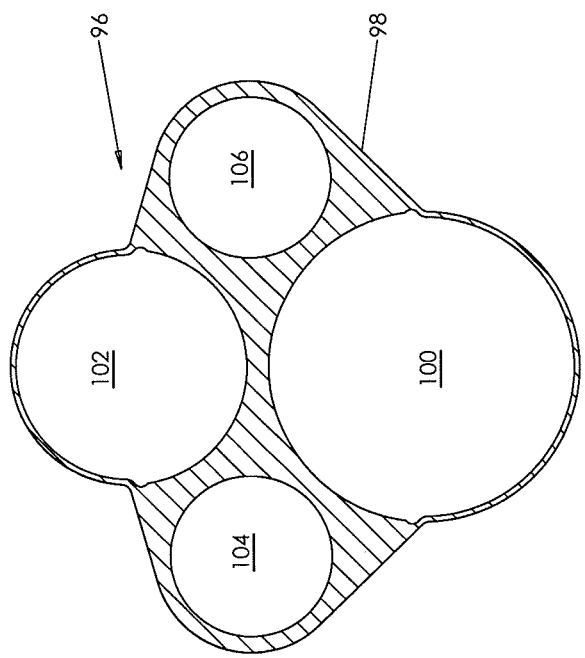
FIG. 18c is a cross-section of the second embodiment of FIG. 18b in a non-collapsed state.
Figure 18B:
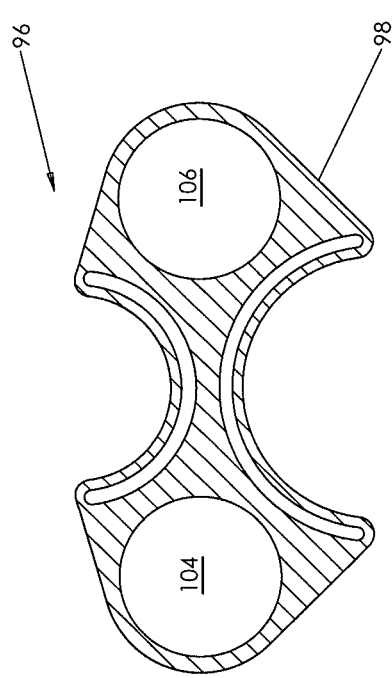
FIG. 18b is a cross-section of a second embodiment of a collapsible inner sheath in a collapsed state.

The embodiment of FIG. 18a includes four lumen 100, 102, 104, 106 that have fixed dimensions. The lumen 100, 102 may be used for inserting an endoscope and tools. The lumen 100, 102 may have different diameters, as shown, or may have the same diameters. Different diameters may provide greater flexibility in relation to the dimensions of tools that may be inserted. The lumen 104, 106 may be flush lumen for supplying and discharging flushing fluid. In some embodiments, the flush lumen 104, 106 may have the additional function for insertion of tools. The diameter of the lumens may be matched with the tools to be introduced, so that radial movement of the tools in the lumens 100, 102 may be minimal. The number of lumens in alternative embodiments may vary from one to more than two. When a tool has to be introduced that has a different diameter, the tool insertion assembly 70 with the inner sheath 96 may be removed from the outer sheath 22 and another tool insertion assembly 70 with lumens having other diameters may be introduced into the outer sheath 22. This may be done without any movement of parts that are in direct contact with brain tissue. Thus the risk of damaging brain tissue may be reduced. FIGS. 18b and 18c show an example of an embodiment in which the inner sheath wall 98 may have a first position and a second position. The inner sheath wall 98 in the first position may have, in cross section, an outer circumference that is convex. In the second position the inner sheath wall 98 may have, in cross section, an outer circumference that includes concave parts so that the total cross sectional area of the inner sheath 96 having its wall 98 in the second position may be reduced relative to the total cross sectional area of the inner sheath 96 having its wall 98 in the first position. This may be especially advantageous for embodiments without an outer sheath 22.

The concept of a sheath having a collapsible wall may also be useful in other minimal invasive surgery applications. In view thereof the disclosure also relates to a minimal invasive surgery assembly comprising at least one insertion assembly including a sheath extending along a longitudinal axis, the sheath having a sheath wall and at least one lumen extending parallel to the longitudinal axis, the sheath wall having a first position and a second position, the sheath wall in the first position having, in cross section, an outer circumference that is convex, and the sheath wall in the second position having, in cross section, an outer circumference that includes concave parts so that the total cross sectional area of the sheath having its wall in the second position is reduced relative to the total cross sectional area of the sheath having its wall in the first position. Introduction of such a sheath in the second, collapsed position reduces the chance of damaging body tissue. When the sheath is in place, it may be brought into the first, non-collapsed position. The chance that the expansion of the sheath after being brought into its desired axial position will cause damage is considerably reduced relative to the chance of causing damage during insertion of the same sheath when it were in a non-collapsed state. Especially in high risk areas, such as the brain tissue but also in other areas, the use of a collapsible sheath that is in a collapsed state during insertion and that is brought into a non-collapsed stated once the desired axial position has been reached may reduce the chance of damaging tissue the operation.

In an embodiment, the collapsible sheath may be biased towards the second position. In yet another embodiment both the first and the second position may be stable positions. Embodiments of collapsible sheaths are the collapsible outer sheath 22 depicted in FIGS. 19a and 19b and the collapsible inner sheath 98 depicted in FIGS. 18b and 18c.

The tool insertion assembly 70 may be rotatable relative to the outer sheath 22 around the longitudinal axis L. A rotation assembly 80, 82, 84, 86, 88 may be present that is configured to facilitate the rotational positioning of the tool insertion assembly 70 relative to the outer sheath 22.

The rotation fixation assembly may include a circular ratchet 80 in one of the tool handling part 72 and the flush assembly main part 52. In the embodiment shown in FIGS. 1-9, the circular ratchet 80 is provided in the flush assembly main part 52. However, in an alternative embodiment, the circular ratchet 80 may be provided in the tool handling part 72. The rotation fixation assembly may include at least one notch 82 that may be connected with the other one of the tool handling part 72 and the flush assembly main part 52. In the embodiment shown in FIGS. 1-9 two notches 82 are provided that are connected with the tool handling part 72. Each notch 82 may have a non-actuated state in which it engages the ratchet 80 thus impeding rotation of the tool insertion assembly 70 relative to the flush assembly 50, and an actuated state in which it does not engage the ratchet 80 thus allowing rotation of the tool insertion assembly 70 relative to the flush assembly 50. Instead of two notches, in an alternative embodiment also one notch 82 or more than two notches 82 may be present. In the alternative embodiment where the ratchet 80 is provided on the tool handling part 72, the notches 82 may be provided in the flush assembly main part 52.

At least one biasing member 84 may be associated with the at least one notch 82. The biasing member 84 may be configured to bias the associated notch 82 into engagement with the ratchet 80. In the embodiment shown in FIGS. 1-9, the biasing member 84 is embodied as a spiral spring. However, the biasing member may also be an integral part of the notch 84 or of a notch member that carriers the notch. For example, the biasing member may be an integral piece of stiff and deflectable material that carries the notch, for example a semi rigid plastic material. Instead of a spiral spring, a blade spring may be feasible as a biasing member 84.

Each notch 82 may be part of notch member 86 that also carries a push button 88 that may be engageable by a human finger. In the embodiment shown, the notches 82 may be brought into the actuated state in which they do not engage the ratchet 80 so that rotation of the tool insertion assembly 70 relative to the flush assembly 50 may be possible. The notch members 86 may be parts that are separate from the tool handling part 72. However, in an alternative embodiment it may also be feasible that the notch members 86 are integrally connected with the tool handling part 72. The tool handling part 72 with the notches 82 may, for example, be formed by injection molding as a single piece of plastic material.

The notches 82 may also have the function of axially fixating the tool insertion assembly 70 relative to the flush assembly 50. The axial fixation may be broken by pushing the push buttons 88. In an embodiment, it may be feasible that the axial fixation may be provided with first notches that may be actuated with first push buttons and that the rotational positioning may be obtained with second notches that may be actuate by second push buttons. A similar effect may be obtained with only one type of notches that may have three positions instead of two.

To facilitate introduction of tools, such as an endoscope, a knife, a scissor and/or a handling tool, into the tool insertion assembly 70, at least one tool insertion channel 90 may be provided. The at least one tool insertion channel 90 may extend from the distal end 74 to the proximal end 76 of the tool handling part 72 and may be funnel shaped with a wide end 92 that may be adjacent the proximal end 76 and a narrow end 94 that may be adjacent the distal end 74 of the tool handling part 72. The narrow end 94 of each insertion channel 90, 90' may emanate into an associated lumen 100, 102 in the inner sheath 96.

Figure 10:
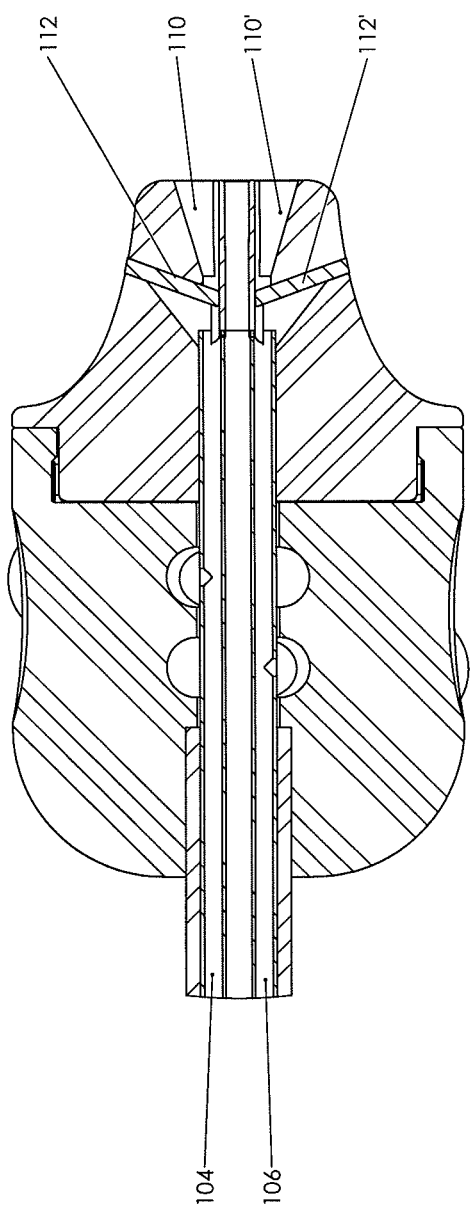
FIG. 10 is a cross section over line X-X in FIG. 6.

In an embodiment, the tool handling part 72 may include at least one additional tool insertion channel 110, 110' extending from a proximal end 76 to a distal end 74 of the tool handling part 72 and emanating in an associated one of the at least one flush lumen 104, 106. A said tool insertion channel 110, 110' may include a valve 112, 112'. FIG. 10 shows the presence of these tool insertion channels 110, 110' and the valves 112, 112'. In a closed position of the valve 112, 112', the valve may prevent that fluid from the flush lumen 104, 106 leaves the neurosurgery assembly 20 via the tool insertion channels 110, 110'. In an open position of the valve 112, 112' a tool may be inserted into the flush lumen 104, 106. Similar valves may also be present in the tool insertion channels 90, 90' that emanate in the tool guiding lumen 100, 102 of the inner sheath. In the embodiment shown, the valves 112, 112' are embodied as flexible flaps that are biased in the position in which they are shown and that may be flexed by a tool that is inserted into tool insertion channels 110, 110'.

The flush assembly main part 52 mentioned before may include at least one ring channel 60, 60' that extends circumferentially around the central passage 58. FIGS. 4, 5, 7, 9 and 10 show the two ring channels 60, 60' of the embodiment that is depicted in FIGS. 1-10. Each ring channel 60, 60' may be formed by an associated portion of the central passage 58 at an axial position of the central passage 58 that has a diameter that is larger than the general diameter of the central passage 58. The flush assembly main part 52 may also include at least one connecting nipple 62, 62' that may be configured to connect a flushing tube. At least one flush channel 64, 64' may extend through the connecting nipple 62, 62' to the associated ring channel 60, 60' and may emanate in the associated ring channel 60, 60'. The embodiment shown in FIGS. 4, 5, 7, 9 and 10 has two ring channels 60, 60'. However, it is also feasible that more than two ring channels are present or that only one ring channel is present. When no flushing is needed the ring channels may be refrained from.

The inner sheath wall 98 may include at least one flush passage 108, 108' extending through the inner sheath wall 98 and emanating in an associated flush lumen 104, 106. The flush passage 108, 108' may be positioned at a longitudinal position of the inner sheath 96 that corresponds with the position of an associated one of the at least one ring channel 60, 60' when the tool handling part 72 is connected to the flush assembly main part 52. Thus a fluid connection may be present between the at least one flush channel 64, 64' extending in the associated connecting nipple 62, 62' and the associated lumen 104, 106. The number of flush passages in the inner sheath wall may vary with the number of ring channels 60, 60' provided in the flush assembly main part 52.

Figure 15:
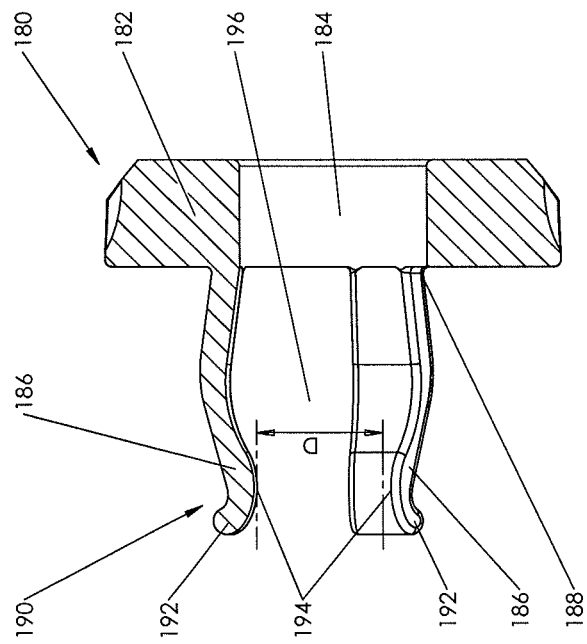
FIG. 15 is a cross section view of the fixation assembly shown in FIG. 14.
Figure 14:
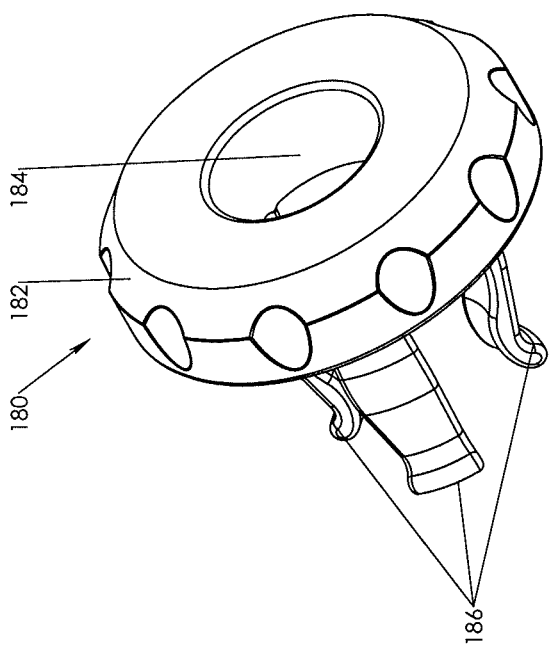
FIG. 14 is a perspective view of another embodiment of a fixation assembly.
Figure 16B:
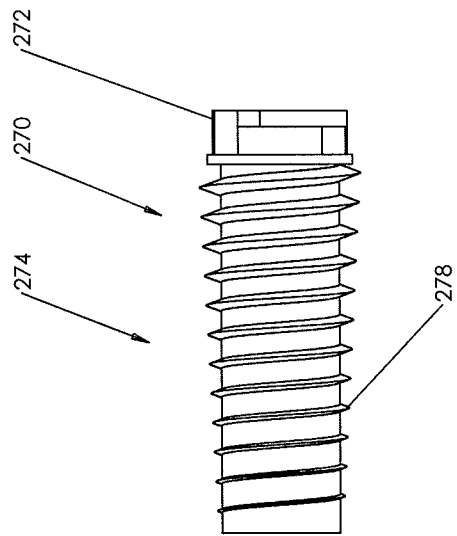
Figure 16A:
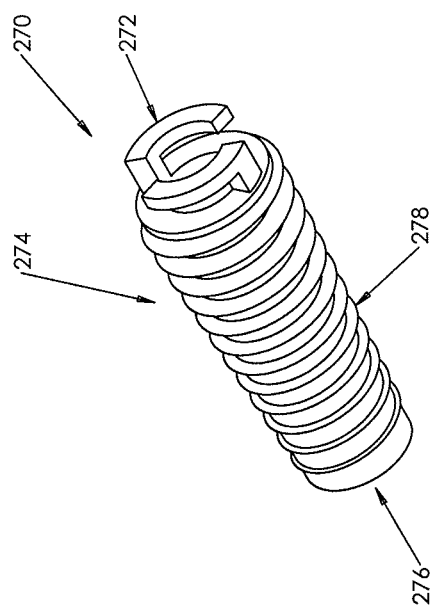
FIG. 16a is a perspective view of another embodiment of a fixation assembly with tapering external screw thread.

The minimal invasive neurosurgery assembly may also include a fixation assembly. A first embodiment of a fixation assembly is indicated with reference number 140 and is shown in FIGS. 1-4 and partly in FIGS. 11-13. A second embodiment of a fixation assembly is indicated with reference number 180 and is shown in FIGS. 14 and 15. A third embodiment is partly shown in FIGS. 16a, 16b and is indicated with reference number 270. The main function of the fixation assembly 140, 180 may be the fixation of the outer sheath 22, or alternatively the inner sheath 96 relative to the skull S of a patient. However, when a force exerted on the sheath 22, 96 exceeds a certain limit, some embodiments of the fixation assembly may allow relative movement of the sheath 22, 96 to the fixation assembly 140, 180, 270. Fixation should not be interpreted literally as allowing no movement at all but not allowing movement below certain limit forces exerted on the outer sheath.

The first embodiment 140 of the fixation assembly may include a skull clamp assembly configured to clamp the fixation assembly 140 on the skull S. Additionally, it may include an sheath clamp assembly 144 configured to clamp the outer sheath 22, or alternatively the inner sheath 96 to the skull clamp assembly in a range of different positions along the longitudinal axis L of the sheath 22, 96.

An example of the various parts of an embodiment of the skull clamp assembly is shown in FIG. 2. The skull clamp assembly may include a central part 146 having a number of flexible legs 148 extending, in a mounted condition parallel to the longitudinal axis L. Each flexible leg 148 may have a distal end 150 with a protrusion 152 that extends radial outwardly. Each flexible leg 148 may have a proximal end 154 that is integrally connected with a distal end of a central bush 156 that has external screw thread 158. The skull clamp assembly may also include a fixation bush 160 having internal screw thread 162 configured to co-operate with the external screw thread 158 of the central bush 156. After drilling a hole in the skull S, the flexible legs 148 may be inserted through the hole so that the protrusions 152 may engage the inner side of the skull S surrounding the hole in the skull. Subsequently, the fixation bush 160 may be turned clockwise to connect the skull clamp assembly to the skull S. The number of flexible legs 148 may vary. The skull clamp assembly may be manufactured from semi rigid plastic material and may be a disposable provided for single use.

Figures 11, 12, 13:
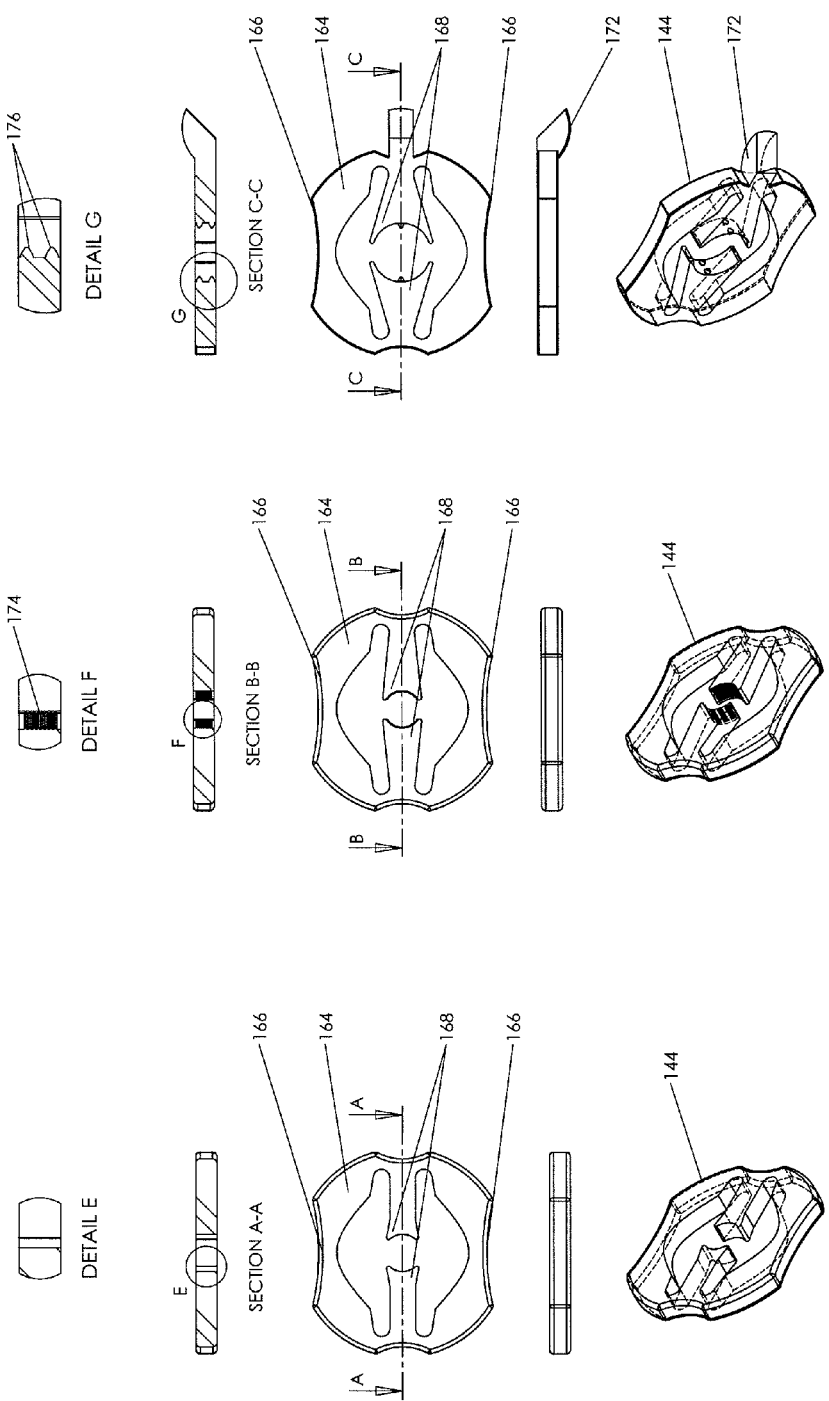
FIG. 11 includes a perspective view, a side view, a top view, a cross section and a detail of the cross section of a first embodiment of a sheath clamp assembly.
FIG. 12 includes a perspective view, a side view, a top view, a cross section and a detail of the cross section of a second embodiment of a sheath clamp assembly.
FIG. 13 includes a perspective view, a side view, a top view, a cross section and a detail of the cross section of a first embodiment of a sheath clamp assembly.

As stated, the first embodiment of the fixation assembly 140 may also include a sheath clamp assembly 144. Embodiments of such a sheath clamp assembly 144 are shown in FIGS. 1, 2, 11, 12 and 13. The sheath clamp assembly 144 may be embodied as a unitary piece of semi-rigid material that may include a circumferential part 164 that may have two diametrically opposed gripping portions 166 on a radial outward peripheral side of the circumferential part 164. The sheath clamp assembly 144 may also have two diametrically opposed clamping fingers 168 extending radial inwardly from a radial inward side of the circumferential part 164. The gripping portions 166 may be positioned relative to the fingers 168 so that a radial inward movement of the gripping portions 166 effected by pressure exerted thereon causes a radial outward movement of the fingers 168. An extensive discussion of such a type of clamping member is given in U.S. Pat. No. 4,901,402. The radial inward side of the clamping fingers 168 may be smooth as shown in FIG. 11. The smooth inward side may be covered with a high friction lining. In an alternative embodiment, the radial inward side of the clamping fingers 168 may have ridges 174 that may co-operate with similar ridges on the outer sheath wall 28 or, alternatively the inner sheath wall 98 as shown in FIG. 12. FIG. 13 shows an embodiment in which the radial inward sides of the clamping fingers 168 carry notches 176 that may co-operate with a range of bayonets 36 that are provided on structure on the outer sheath wall 28 as shown in FIG. 2 or, alternatively the inner sheath wall 98.

The central part 146 of the fixation assembly 140 may have a bayonet connector 170 on a proximal end 172 of the central bush 156. The bayonet connector 170 and the fingers 168 may be configured to co-operate so that the sheath clamp assembly 144 may be releasably mountable on the central part 146. This configuration is visible in the embodiment shown in FIG. 2. Of course, the bayonet connection is just one example and other connection mechanisms are possible.

In an alternative embodiment, the sheath clamp assembly 144 and the central part 146 may be a single unitary piece.

FIGS. 14 and 15 show an alternative embodiment of a fixation assembly 180. That embodiment may include a ring part 182 with a central opening 184. The fixation assembly 180 may also have a number of flexible legs 186 of which a proximal end 188 may be connected with the ring part 182. Each leg 186 may extend, in a mounted condition substantially parallel to the longitudinal axis L. Each flexible leg 186 may have a distal end 190 with a protrusion 192 that extends radial outwardly. The legs 186 may be positioned relative to each other so that radial inward sides 194 of the legs 186 define a sheath passage 196 of which the diameter D is so small that, in a mounted condition of the fixation assembly 180 in a hole in the skull S and in a mounted condition of the outer sheath 22 or, alternatively the inner sheath 96 the radial inward sides 194 of the legs 186 may engage the sheath 22, 96 to maintain the sheath 22, 96 in a stable position relative to the fixation assembly 180.

A third embodiment of the fixation assembly 270, of which an example is shown in FIG. 16, may include a bush 274 having a central passage 276 through which the outer sheath 22 or, alternatively the inner sheath 98 may be insertable. The bush 274 may have external screw thread 278 that may be configured to directly engage the skull material bounding the hole in the skull. The screw thread 278 may be tapering as shown. Alternatively or additionally, the bush 274 may be tapering. The fixation assembly 270 may include means for clamping or fixating the outer sheath 22 or, alternatively the inner sheath 96. Such means may include sheath clamping fingers that may engage the outer sheath wall 28 or, alternatively the inner sheath wall 98. Alternatively, the means may include a sheath clamp assembly 144 that may be mounted on the bush 274 via bayonet 272 and of which examples are depicted in FIGS. 11-13.

It will be clear that the sheath clamp assembly may be embodied in numerous ways. It may also be embodied as clamp that includes more than just one part and, for example, resemble a clothes peg. It may be advantageous when the sheath clamp assembly is embodied so that the clamp assembly may be released with a single hand. The sheath clamp assembly may also be provided with a mechanism that provides a clicking noise when the sheath 22, 96 is moved longitudinally along the sheath clamp assembly. Such a mechanism may, for example, be provided by a relief structure on the outer sheath 22 and by a flexible finger that engages the relief structure and makes noise when the relieve finger is moved over the relief structure. Each click of the finger may indicate a certain distance of movement.

In order to help the surgeon to establish to what distance he has introduced the outer sheath 22, or alternatively the inner sheath 96 into the brain, the neurosurgery assembly 20 may include an insertion depth indicator 172 that may indicate a character that may be indicative for the insertion depth of the outer sheath 22 or, alternatively the inner sheath 96. In an embodiment, the insertion depth indicator 172 may be configured so that it is visible from a proximal end of the neurosurgery assembly 20 when looking in the direction of a distal end of the neurosurgery assembly 20. In an embodiment the outer sheath 22 or, alternatively the inner sheath 96 may have a scale with numbers on the sheath wall 28, 98. An embodiment of the insertion depth indicator 172 may include optical prism and a lens (see FIGS. 1, 2 and 13) that may project the scale 38 that is present on the outer sheath 22 (see FIGS. 1 and 2) or, alternatively inner sheath 96 in a direction along the longitudinal axis in the proximal direction. In the embodiments shown in the Figs., the optical prism and lens 174 are provided on the sheath clamp assembly 144. In an alternative embodiment such a prism may be provided in the flush assembly main part 52. Also other embodiments, such as a wheel that may have numbers on its outer circumference and that may be provided on the fixation assembly 140, 180, 270 and that may engage the outer wall 28 of the outer sheath 22 or, alternatively the inner sheath wall 98 and that may rotate when the sheath 22, 96 is moved axially, may be feasible as an insertion depth indicator 172. The wheel may be in the zero position when the assembly is unpacked from its package. Alternatively, the wheel may be in the zero position when the distal end of the sheath 22, 96 is at the level of the skull.

Figure 17:
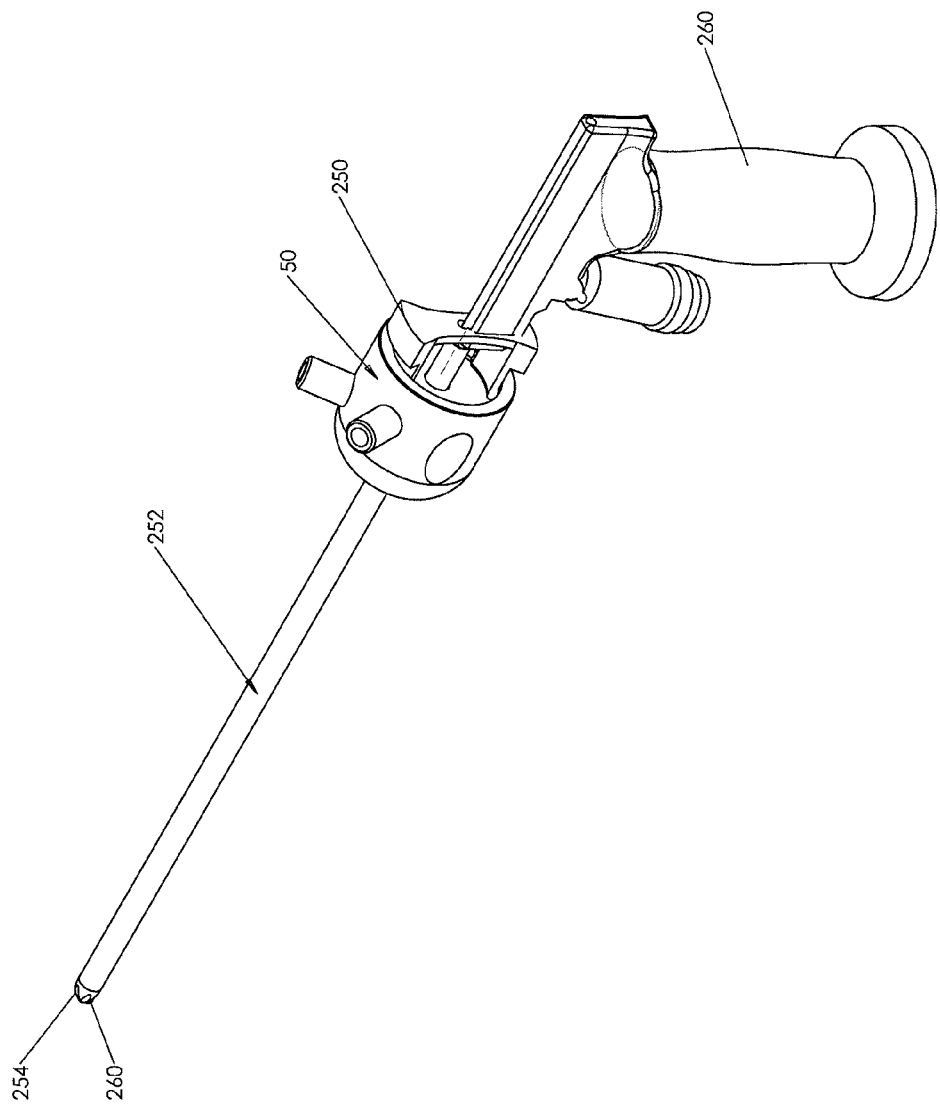
FIG. 17 shows a connector that connects an inner sheath with an endoscope.

During the operation, it may be useful to be able to axially fixate the endoscope or a tool relative to the inner sheath 96. Especially in an embodiment without an outer sheath 22 that may be useful. The endoscope may then be steered by the surgeon. The inner sheath 96 will automatically follow the movements of the endoscope. An example of an embodiment of the connector 250 is shown in FIG. 17. The connector 250 is clearly visible as well as the inner sheath 252, the lumen 254 therein and the endoscope 260. It will be clear that the connector 250 may also be used to axially fixate tools relative to the inner sheath 96.

The neurosurgery assembly may include more than one tool insertion assembly 70. The main difference between the various tool assemblies may be the embodiment of the inner sheath 96, more particularly the number and dimensions of the lumen in the inner sheath 96. For introducing different tools or different endoscopes, different lumen diameters may be necessary. To that end, the tool insertion assembly 70 may be exchanged by another one, while leaving the outer sheath 22 in place.

One embodiment of the tool insertion assemblies 212, of which an example is shown in FIGS. 23a and 23b, may a have tool handling part 72 that is connected with an inner sheath 214 that is, in fact, a dummy inner sheath 214 of which at least a distal end 216 may be closed off. The dummy inner sheath 214 may be a solid piece of material having no lumen. The length of the dummy inner sheath 214 may be so that in a mounted condition of the dummy tool insertion assembly 212 on the flush assembly main part 52, the distal end 216 of the dummy inner sheath 214 also closes off the distal opening 32 of the outer sheath 22. The distal end 216 may have a rounded tip. The outer sheath 22 may be introduced into the brain of the patient when the tool insertion assembly 212 with the dummy inner sheath 214 is placed in the outer sheath 22 and the tool handling part 72 is connected with the flush assembly main part 52. Thus the risk of damaging the brain of the patient may be reduced.

Figure 24:
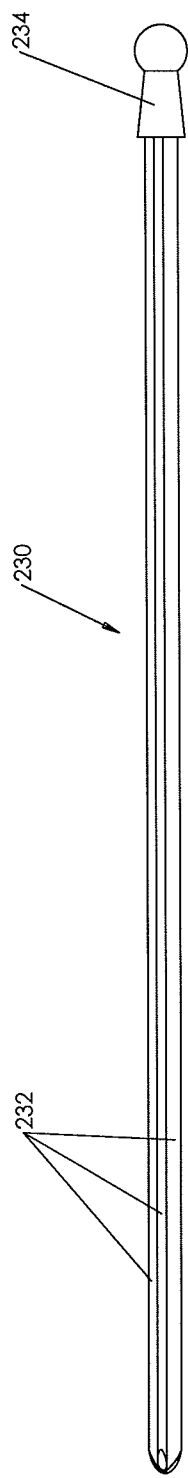
FIG. 24 is elevation view of an embodiment dummy tool that may be inserted in an inner sheath.

For embodiments without an outer sheath 22, a similar advantage may be obtained by using a dummy tool 230. An example of such a dummy tool is shown in FIG. 24. The dummy tool 230 may include a number of dummy tool inserts 232 that may be inserted in associated lumen 100, 102, 104, 106, 200, 202, 209 of an inner sheath 96 when the inner sheath 96 may be inserted into the brain. In one embodiment of the dummy tool 230, the dummy tool inserts 232 may be solid. In another embodiment of the dummy tool, at least one of the dummy tool inserts 232 may include a lumen of which the distal end 236 may be closed off. The length of the at least one dummy tool insert 232 may be such that in a mounted condition of the dummy tool 230 on the tool handling part 72, the distal end 234 of the at least one dummy tool insert 232 also closes off the distal opening of an associated one of the at least one lumens 100, 102, 104, 106, 200, 202, 209. The dummy tool 230 may also include a gripping piece 234 for an easy handling of the dummy tool 230.

An embodiment of the neurosurgery assembly may have a pressure sensor 220 for measuring the pressure fluid in a cavity in the brain. The pressure sensor 220 may, for example, be mounted adjacent the distal tip of an inner sheath 96, 214. The term "adjacent" is also meant to include "at" and "on". For example, the dummy sheath 214 or dummy insert 232 may carry such a pressure sensor 220 (see FIG. 23b). Electrical wiring 222 may extend through the dummy sheath 214 or dummy insert 232. When penetrating a cavity in the brain, the pressure of the fluid being present in that cavity may be directly measured. In an alternative embodiment, the pressure sensor may also be part of the flush assembly main part 52. Such a sensor may be used for measuring the pressure of flushing fluid. An assembly of more than one pressure sensors is also feasible. In yet a further alternative embodiment the pressure sensor 222 may measure the pressure exerted by the brain tissue on the tip of the dummy sheath 214 when the outer sheath 22 with the dummy sheath 214 is inserted into the brain. A resistance force that is too great may indicate that brain area may be penetrated that should not be penetrated. A thrust force increase may indicate that a cavity membrane may be engaged.

Instead of removing the tool insertion assembly 70 having lumens 100, 102 with fixed diameters, another embodiment of the tool insertion assembly may include an inner sheath 96 having a lumen 200, 202 that may be bounded by at least one flexible wall part 204, 206, 208, 210. Examples of cross sections of inner sheath with flexible wall parts are shown in FIGS. 20-23. The flexible wall part 204, 206, 208 may have a single stable first position towards it may be biased. In another embodiment the flexible wall part may have more than one stable position, for example, at least a stable first and a stable second position. Depending on the intermediate position of the flexible wall part 204, 206, 208 it may be biased either to the stable first or the stable second position. The lumen 200, 202 may be fit for accommodating without substantial radial play a tool having a first diameter D1 for lumen 200 and D3 for lumen 202 when the at least one flexible wall part 204, 206, 208 is in the stable first position. The lumen 200 may be fit for accommodating without substantial radial play a tool having a second diameter D2 for lumen 200 that may be different from the first diameter D1. In the embodiment with two stable positions, the lumens 200 and 202 may then have their at least one flexible wall part 204, 206, 208 in the stable second position.

It will be clear that also one lumen with a flexible wall part is feasible or more than two lumens with flexible wall parts are feasible.

In an embodiment having at least two lumen 200, 202, at least a first lumen 200 that may accommodate tools having different diameters without substantial radial play, may have a flexible wall part 204. In one embodiment, the flexible wall part 204 may have a single stable first position towards it may be biased. The first lumen 200 may have a large cross section condition that is substantially circular when the flexible wall part 204 is moved out of the stable first position and the first lumen 200 may have a small cross section condition that is substantially non-circular when the flexible wall part 204 is in the stable first position towards which it may be biased. In another embodiment, the flexible wall part 204 may have at least a first and a second stable position or even more stable positions. In the embodiment wherein the flexible wall part 204 has two stable positions, the first lumen 200 may have a large cross section condition that may substantially circular when the flexible wall part 204 is in the second stable position and the first lumen 200 may have a small cross section condition that is substantially non-circular when the flexible wall part 204 is in the first stable position.

The flexible wall part 204 may be an intermediate wall part separating the first and second lumen 200, 202 so that when the first lumen 100 is in a condition with decreased cross section, the second lumen 102 is in a condition with increased cross section and vice versa.

In an alternative embodiment, the flexible wall part 206, 208 may be not an intermediate wall part and thus not separate a first and a second lumen 200, 202.

Figure 20:
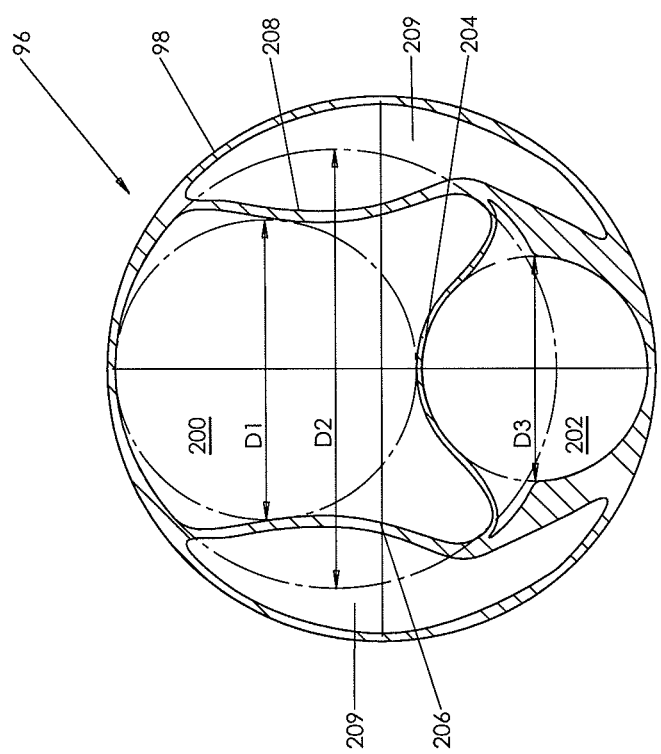
FIG. 20 is a cross section of a third embodiment of an inner sheath.
Figure 21:
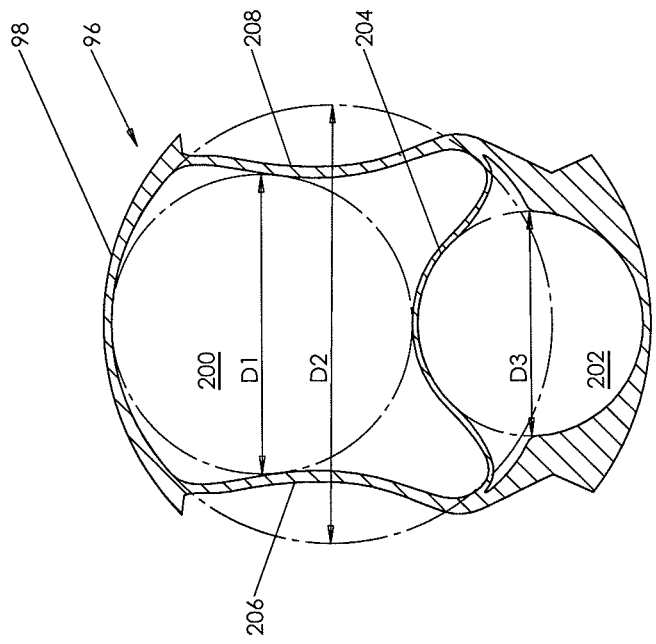
FIG. 21 is a cross section of a fourth embodiment of an inner sheath.
Figure 22:
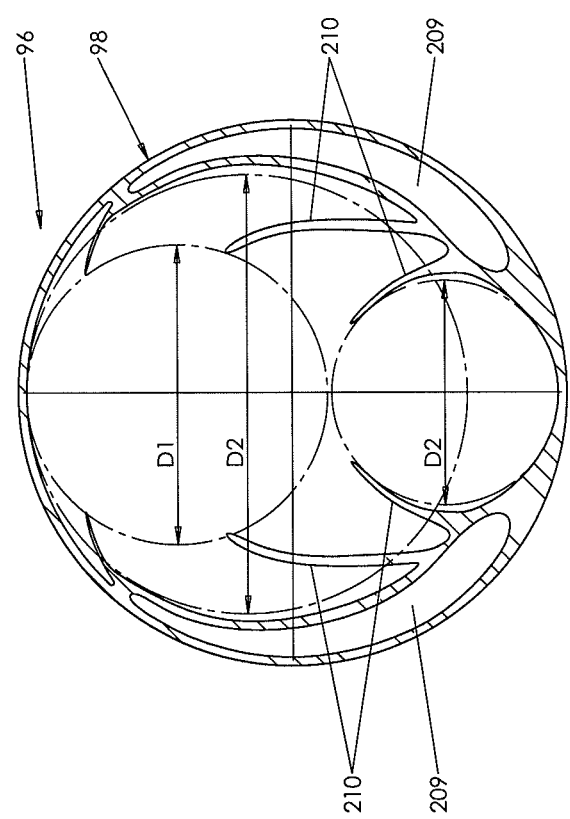
FIG. 22 is a cross section of a fifth embodiment of an inner sheath.

In yet another embodiment at least one of the first and the second lumen 200, 202 may have, in addition to the flexible intermediate wall part 204, at least one further flexible wall part 206, 208 that may have at least a first stable position to which the flexible wall part 206, 208 may be biased. An example of such an embodiment is shown in FIGS. 20 and 21. The embodiments of FIGS. 20 and 21 differ in that the inner sheath wall 98 is circular in the embodiment of FIG. 20 so that the inner sheath 96 also includes two flush lumens 209. In the embodiment of FIG. 21 the flush lumen are not included in the inner sheath 96. The flush lumen may be formed by the flexible wall parts 206, 208 and the outer sheath wall 28 when the inner sheath 96 is inserted into the outer sheath 22.

The flexible wall parts 210 may also be connected with only one end to the inner sheath 96, thus forming flexible flaps 210. Depending on the position of flexible wall parts 210, tools and endoscopes of varying diameter may be introduced.

Figure 25:
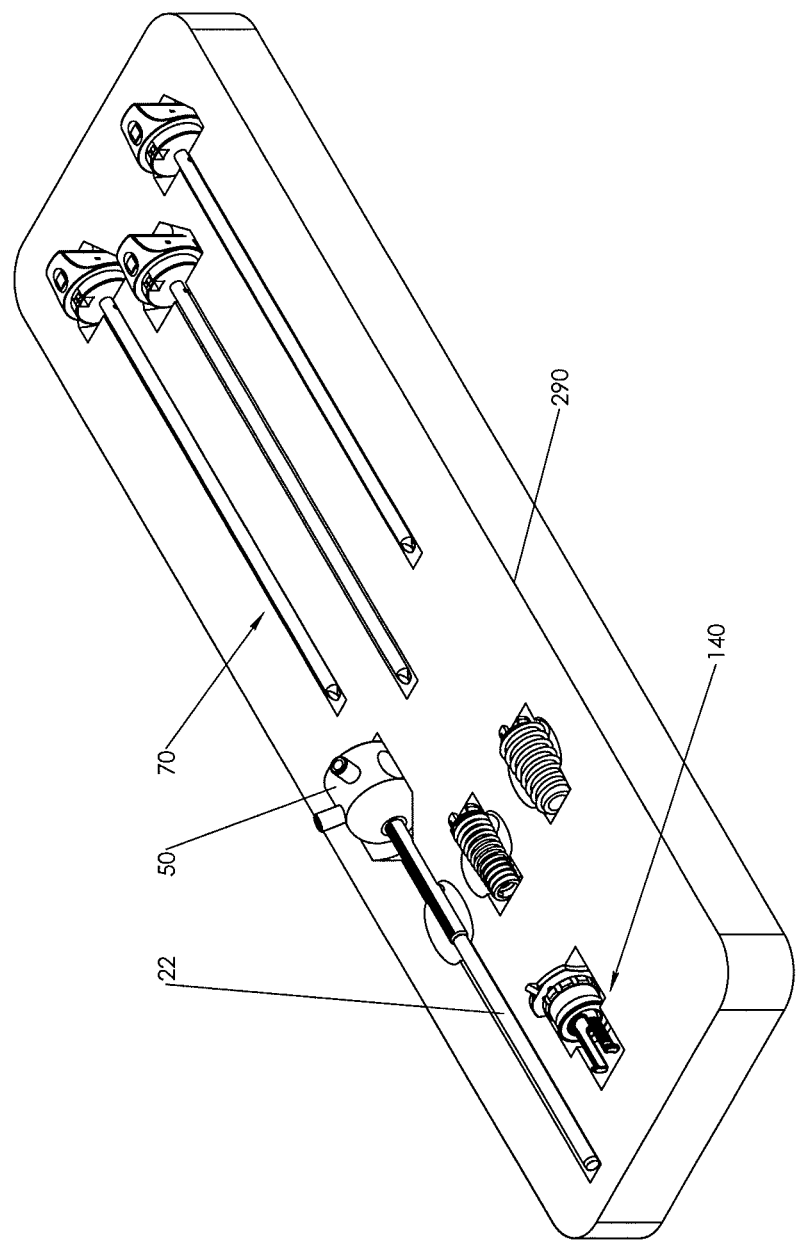
FIG. 25 is a perspective view of a package with an embodiment of a neurosurgery assembly.

FIG. 25 shows an example of an embodiment of a kit of parts including a single outer package 290 that contains a neurosurgery assembly in a sterilized atmosphere. The outer package 290 of the example shown includes a flush assembly 50 with an outer sheath 22, a fixation assembly 140 and three tool insertion assemblies 70 of which one may be a dummy tool insertion assembly. It will be clear that numerous variations are possible. Preferably, the ordering of the various parts in the package 290 is such that it corresponds with the order in which the various parts have to be used during the operation. This may reduce the chance of mistakes during the operation.

As stated before with respect to some of the parts of the neurosurgery assembly, it should be noted that the outer sheath 22, the flush assembly 50, the tool insertion assembly 70 and the fixation assembly 140; 180 may substantially be manufactured from plastic so that the neurosurgery assembly is disposable after single use. It is clear that also other materials may be used, while maintaining the single use and disposability aspect.

INDUSTRIAL APPLICABILITY

The minimal invasive neurosurgery assembly 20 may be applied for performing minimal invasive neurosurgery on the brain, for example, for relieving fluid pressure from a brain cavity, for visual inspection of a brain with an endoscope, for taking a biopsy or for operating on brain tissue, e.g. the removal of a tumor.

In general terms a method for performing a neurosurgery operation on the brain may include:
  providing the neurosurgery assembly 20 as described above;
  determining a region in which the operation has to be performed and based on that determining a position at which a hole has to be drilled in the skull;
  drilling a hole in the skull;
  inserting an inner sheath 96 of the assembly 20 through the hole; and
  inserting at least one of an endoscope and a tool into the tool insertion assembly 70 through an associated tool insertion channel 90, 110 into an associated one of the lumen 100, 102, 104, 106 of the inner sheath 96.

In an embodiment of the method in which the neurosurgery assembly has the additional features of a fixation assembly 140, 180, 270 and an outer sheath 22, the method may additionally include:
  connecting the fixation assembly 140, 180, 270 to the skull of the patient after drilling the hole; and
  connecting the outer sheath 22 to the fixation assembly 140, 180, 270 to keep it stationary relative to the skull.

The connecting of the outer sheath 22 to the fixation assembly 140, 180, 270 may be effected directly, for example via the sheath clamp assembly 144, or indirectly, for example via the flush assembly that may be connectible directly to the fixation assembly 140, 180, 270.

In an embodiment of the method in which the neurosurgery assembly has the additional feature of a fixation assembly 140, 180, 270 but in which no outer sheath is provided, the method may include:
  connecting the fixation assembly 140, 180, 270 to the skull of the patient after drilling the hole; and
  connecting the inner sheath 96 to the fixation assembly 140, 180, 270 to keep it stationary relative to the skull.

Again, the connecting of the inner sheath 96 to the fixation assembly 140, 180, 270 may be effected directly, for example via the sheath clamp assembly 144, or indirectly, for example via the flush assembly that may be connectible directly to the fixation assembly 140, 180, 270.

First the region of the brain that needs treatment may be determined using various diagnostic techniques such as MRI- and CT-scans. Subsequently, a position on the skull may be determined where a hole has to be drilled. After formation of the hole in the skull, the skull clamp assembly including the central part 146 and the fixation bush 160 of the fixation assembly 140 may be placed into the hole in the skull. To that end, the flexible legs 148 of the central part 146 may be inserted into the hole in the skull until the protrusion 152 may engage the inner surface of the skull surrounding the hole. Subsequently, the fixation bush 160 may be tightened so that the central bush 156 and the fixation bush 160 will be fixated on the skull. Next the sheath clamp assembly 144 may be connected to the bayonet connector 170. As stated before, the sheath clamp assembly 144 may, alternatively, be an integral part of the skull clamp assembly. By pushing the gripping portions 166 together, the clamping fingers 168 may be moved radial away from each other. In that state, the outer sheath 22 may be moved through the central opening of sheath clamp assembly 144 and the central passage in the central part 146 and be inserted in the brain tissue. The distal opening 32 of the outer sheath 22 may be closed off by the dummy inner sheath 214 of the dummy tool insertion assembly 212 in order reduce the chance of damaging brain tissue. The dummy inner sheath 214 may include a lumen for accommodating an endoscope and the distal end 216 may be closed off by the optical element 218. The lumen of the dummy inner sheath 214 may contain an endoscope so that the region surrounding the distal end 216 may be inspected via the optical element 218 during insertion of the outer sheath 22. When the distal end 24 is in the desired region of the brain, the pushing force on the gripping portions 166 may be relieved. As a consequence, the clamping fingers 168 may move radial inward towards each other and engage the outer sheath wall 28, thus fixating the outer sheath 22 in the desired position.

In the embodiment of the fixation assembly 180 after drilling the hole in the right position of the skull, the flexible legs 186 may be inserted into the hole until the protrusion 192 engage the inner surface of the skull surrounding the hole. To help the insertion of the flexible legs 186 into the drilled hole, the fixation assembly 180 may be rotated by rotating the ring part 182. When the fixation assembly 180 is positioned in the hole in the skull, the outer sheath 22 may be inserted via the sheath passage 196 into the brain tissue. The flexible legs 186 will exert a clamping force on the outer sheath wall 28. Thus, when the distal end 24 of the outer sheath 22 is in the desired region in the brain, no additional support of the outer sheath 22 is necessary to keep it in that position. Also when using this embodiment of the fixation assembly 180, the distal opening 32 of the outer sheath 22 may be closed off by the dummy sheath 22 of dummy tool insertion assembly 212.

Alternatively, the fixation assembly 270 with the bush 274 with external screw thread 278 may be used. That fixation assembly 270 may be screwed into the hole in the skull. Subsequently, the outer sheath may be inserted and clamped by the sheath clamping fingers 280 or a similar sheath clamp assembly 144 that may be connected to the fixation assembly 270.

As explained in the detailed description, an embodiment of the neurosurgery assembly may not have an outer sheath 22. For those embodiments placement of a fixation assembly may not be necessary. The inner sheath 96 with the flush assembly main part 52 may be connected with the endoscope 260 by the connector 250 and during the operation the endoscope may be held in the hands of the surgeon. Alternatively, a fixation assembly 140, 180, 270 may be used to which the flush assembly main part 52 is connected or connectible. This may provide the advantage that the flush assembly main part 52 and the flushing fluid supply and discharge tubes connected thereto may remain stationary and not obstruct or impede the freedom of movement of the surgeon. When the inner sheath 96 of the embodiments without the outer sheath 22 is inserted into the brain, the distal openings of the lumen 100, 102, 104, 106, 200, 202, 209 may be closed off by the dummy tool inserts 232 of the dummy tool 230. After introduction of the inner sheath 96 into the brain tissue, the dummy tool 230 may be removed. Because the distal openings of the lumen may be closed off during insertion, damage of brain tissue during insertion may be reduced.

When inserting the outer sheath 22 or, alternatively the inner sheath 96 into the brain tissue, the surgeon may use the scale 38 on the outer sheath 22 or, alternatively on the inner sheath 96, to determine to what extend or depth the sheath 22, 96 protrudes into the brain tissue. The scale 38 may be visible from the proximal side when looking in the longitudinal axis by using the insertion depth indicator 172. Thus, the surgeon does not have to move his head from the position in which he may inspect the endoscope image to the side for reading the scale 226. Instead, he may keep his head in the same position during insertion of the outer sheath 22 and alternatingly look at the endoscope image and the insertion depth indicator 172.

In an embodiment of the method in which the outer sheath 22 is collapsible in that the outer sheath wall 28 has a first position in which, in cross section, the circumference of outer sheath wall 28 is convex, and has a second position in which, in cross section, the circumference of the outer sheath wall includes concave part so that the cross sectional area of the outer sheath 22 is reduced, the method may include:
 inserting the outer sheath 22 into the skull when the outer sheath wall 28 is in the second position in which the outer sheath wall 28 has, in cross section, an outer circumference that includes concave parts so that the total cross sectional area of the outer sheath is reduced; and after the inserting
 bringing the outer sheath wall 28 into the first position in which the outer sheath wall 28 has, in cross section, an outer circumference that is convex.

In other words, in order to minimize damage to brain tissue the outer sheath 22 may be brought in a collapsed condition as shown in FIG. 19a. The reduced cross sectional area may reduce the damage to the brain tissue. After introduction, the outer sheath 22 may be brought in the non-collapsed condition as shown in FIG. 19b, for example, by inserting a tool insertion assembly 70 therein.

For the embodiment without the outer sheath 22, a similar effect may be obtained when a collapsible inner sheath 96 embodiment is used of which an example is shown in FIGS. 18b and 18c. In an embodiment of the method using such an neurosurgery assembly 20 may include:
 inserting the inner sheath 96 into the skull when the inner sheath wall 98 is in the second position in which the inner sheath wall 98 has, in cross section, an outer circumference that includes concave parts so that the total cross sectional area of the inner sheath 96 is reduced; and after the inserting
 bringing the inner sheath wall 98 into the first position in which the wall 98 has, in cross section, an outer circumference that is convex.

In other words, the inner sheath 96 may be introduced into the brain tissue in the collapsed condition as shown in FIG. 18*b*. Once inserted and in place, the inner sheath 96 may be brought in the non-collapsed state, for example, by introducing tools into the lumens 100, 102.

In an embodiment of the method, in which the neurosurgery assembly 20 includes the flush assembly 50 with the at least one ring channel 60, 60' and the at least one connecting nipple 62, 62', the method may include:

connecting at least one flushing tube to the at least one connecting nipple 62, 62';

supplying flushing fluid via the at least one flush channel 64, 64' to the associated ring channel 60, 60', the at least one flush passage 108, 108' in the inner sheath wall 98 and into the associated flush lumen 104, 106; and manipulating at least one of an endoscope or a tool inserted into the tool insertion assembly 70 during supplying flushing fluid while keeping the flush assembly main part 52 stationary.

Before or after inserting the sheath 22, 96 into the brain tissue, the connecting nipples 62, 62' may be connected to tubes that may supply and discharge flushing fluid. Because, during operation, the flush assembly main part 52 will be substantially stationary, the tubes may be substantially stationary as well, even when the surgeon manipulates the endoscope and the tools.

Next, the dummy tool insertion assembly 212 may be removed from the outer sheath 22. That may be done by pushing on push buttons 88 on the tool handling part 72, while simultaneously exerting a pulling force on the tool handling part 72 along the longitudinal axis in a proximal direction. After removal of the dummy tool insertion assembly 212 a tool insertion assembly 70 may be inserted in the outer sheath 22 via the central passage 58 of the flush assembly main part 52. The tool insertion assembly 70 may have an inner sheath 96 with lumens 100, 102 of different diameters. The tool insertion assembly 70 may be selected on the basis of the diameters of the lumens 100, 102 and the tools or endoscope that the surgeon wishes to use. The first flush lumen 104 may be used for supplying flushing fluid and the second flush lumen 106 may be used for discharging flushing fluid. When the tool insertion assembly 70 is in its proper position in the outer sheath 22, the flush passages 108, 108' may be in line with the ring channels 60, 60'. Thus a fluid communication is present between the first flush lumen 104, the flush passage 108, the ring channel 60 and the flush channel 64 that may be connected to a flushing fluid supply tube via connecting nipple 62. A similar fluid communication may be present between the second flush lumen 106, the flush passage 108', the ring channel 60' and the flush channel 64' that may be connected to a flushing fluid discharge tube via connecting nipple 62'. Thus flushing of the relevant region may be performed.

Alternatively, for the embodiments without the outer sheath 22, the dummy tool 230 may be removed from the inner sheath 96 by exerting a pulling force on the dummy tool gripping piece 234 and by holding the tool handling part 72 in place in the flush assembly main part 52.

After the tool insertion assembly 70 is inserted, an endoscope and one or more tools may be introduced via the funnel shaped tool insertion channels 90, 90' into the lumens 100, 102 of the inner sheath 96. The diameters of the endoscope and the tools preferably match with the diameters of the lumens 100, 102 so that substantially no radial play is present between the tools and the associated lumen 100, 102 or the endoscope and the associated lumen 100, 102. Consequently, a stable tool control and a stable image via the endoscope may be obtained. The tools and the endoscope may be pointed in other directions in the relevant region of the brain by rotating the inner sheath 96 by rotating the tool handling part 72. To that end, the push buttons 88 on the tool handling part 72 may have to be pushed in so that the notches 86 are brought out of engagement with the circular ratchet 80. Subsequently, the tool handling part 72 and the inner sheath connected to it may be rotated. The notches 86 and the circular ratchet 80 may be also be embodied so that above a certain limit torque, exerted on the tool handling part 72 in the one direction and on the flush assembly main part 52 in the other direction, rotation of those relative to each other may be effected. This may prevent inadvertent rotation of the tool insertion assembly 70 relative to the flush assembly 50. The relative rotation may produce a clicking noise by the interaction of the notches 86 and the ratchet 80. These clicks may help the surgeon to control his handling of the tool handling part 72. Such rotation may be effected without movement of parts of the neurosurgery assembly relative to brain tissue that are in direct contact with brain tissue. Thus the chance of damaging brain tissue is reduced. Also the tools and the endoscope may be moved axially when the distal end 24 of the outer sheath 22 is in a brain cavity without movement of neurosurgery parts relative to brain tissue that are in direct contact with brain tissue. Consequently, also during axial movement of the endoscope and the tools inserted in the inner sheath 96, the chances of damaging brain tissue is minimized.

When the surgeon whishes to use tools or an endoscope having a different diameter that does not correspond with the diameter of one of the lumens 100, 102 of the inner sheath 96, the tool insertion assembly 70 may be removed and replaced by another tool insertion assembly 70 of which at least one of the lumens 100, 102 has the required diameter.

The flexibility of the system may be even greater when a tool insertion assembly 70 is used having at least one lumen 200, 202 of which the cross section area may be varied by means of a flexible wall part 204, 206, 208, 210 that may have at least a single stable position or two or more stable positions. The frequency of exchanging tool insertion assemblies 70 during operation may be reduced when using the flexible wall type insertion tool assemblies.

An embodiment of the method using such a neurosurgery assembly may include:

inserting the tool having a first diameter into the lumen 200, 202 that is bounded by at least one flexible wall part 204, 206, 208 and that is biased towards a stable first position, the tool having the first diameter being accommodated without play when the at least one flexible wall part 204, 206, 208 is in the stable first position; and inserting the tool having a second diameter that is different from the first diameter in the lumen 200, 202 that is bounded by at least one flexible wall part 204, 206, 208 thereby bringing the flexible wall part out of the first position towards which it is biased so that the tool having the second diameter is accommodated without substantial play in the lumen 200, 202 with the at least one flexible wall part 204, 206, 208.

One of the advantages of the disclosed minimal invasive neurosurgery assembly is that it may be a single use, disposable assembly. The endoscope that may be used together with the neurosurgery assembly does not have to include lumen for flushing fluid or for guiding tools. Thus the cleaning and sterilization of the endoscope may be much easier because only the outside of the endoscope has to be cleaned and sterilized. The lumens that may be contaminated are part of the neurosurgery assembly that may only be used once. Of course, it is not excluded that the neurosurgery assembly is used more than once. That may depend on the costs of the assembly and the costs of sterilizing such an assembly as well as the valuation of the increased safety when using the neurosurgery assembly only once.

In order to limit the number of claims, some aspects that may be relevant have not been claimed in dependent claims. In order to have the claim language of those aspects available in this disclosure the following is included:

32. The neurosurgery assembly according to claim 8, wherein rotation fixation assembly includes:
    a circular ratchet in one of the tool handling part and the flush assembly main part; and
    at least one notch connected with the other one of the tool handling part and the flush assembly main part,
    the at least one notch having a non-actuated state in which it engages the ratchet thus impeding rotation and preventing axial movement of the tool insertion assembly relative to the outer sheath, and the at least one notch having an actuated state in which it does not engage the ratchet thus allowing axial movement and rotation of the tool insertion assembly relative to the outer sheath.
33. The neurosurgery assembly according to claim 32, including:
    at least one biasing member associated with the at least one notch configured to bias the associated notch into engagement with the ratchet.
34. The neurosurgery assembly according to claim 32 or 33, wherein each notch is part of notch member that also carries a push button that is engageable by a human finger.
35. The neurosurgery assembly according to any one of claims 1-23, wherein the at least one tool insertion channel is funnel shaped and has wide end that is adjacent the proximal end and a narrow end that is adjacent the distal end of the tool handling part.
36. The neurosurgery assembly according to claim 35, the narrow end of the at least one tool insertion channel emanating into an associated one of the at least one lumen in the inner sheath.
37. The neurosurgery assembly according to any one of claims 12-15, wherein the sheath clamp assembly and the skull clamp assembly are a unitary piece.
38. The neurosurgery assembly according to any one of claims 12-15, wherein the skull clamp assembly has a bayonet connector, the bayonet connector and the fingers being configured to co-operate so that the sheath clamp assembly is releaseably mountable on the skull clamp assembly.
39. The neurosurgery assembly according to claim 14, wherein the external screw tread is a tapering thread of which the diameter increases from a distal end to a proximal end.
40. The neurosurgery assembly according to claim 17, wherein at least a first lumen of the at least two lumen having different diameters has a flexible wall part, the flexible wall part having at least a first stable position, the first lumen having a large cross section condition that is substantially circular when the flexible wall part is moved out the first stable position, the first lumen having a small cross section condition that is substantially non-circular when the flexible wall part is in the stable first position.
41. The neurosurgery assembly according to claim 40, wherein the flexible wall part is an intermediate wall part separating the first and second lumen so that when the first lumen is in a condition with a decreased cross section, the second lumen is in a condition with an increased cross section and vice versa.
42. The neurosurgery assembly according to claim 41, wherein at least one of the first and the second lumen has, apart from the flexible intermediate wall part, at least one further flexible wall part that has at least one stable, first position.
43. The neurosurgery assembly according to any one of claims 18, 40-42, wherein the first lumen may accommodate substantially without radial play tools having at least two different diameters depending on the position of at least the at least one flexible wall part (204, 206, 208, 210) of the first lumen.
44. The neurosurgery assembly according to claim 19, wherein the distal end of the dummy inner sheath has a rounded tip.
45. The neurosurgery assembly according to claim 20, wherein the distal end of the dummy tool insert has a rounded tip.
45. The neurosurgery assembly according to any one of claims 1-23 and 32-44, the outer sheath, the flush assembly, the tool insertion assembly and the fixation assembly substantially being manufactured from plastic so that the neurosurgery assembly is disposable after single use.

The various features described in combination for certain embodiments may be applied separate from each or in other combinations so as to form other embodiments.

It will be apparent to those having ordinary skill in the art that various modifications and variations can be made to neurosurgery assembly and the method as disclosed herein. Other embodiments will be apparent to those having ordinary skill in the art from consideration of the specification. For example, although the neurosurgery assembly is especially suitable for neurosurgery on the brain, it may be used for other applications than neurosurgery on the brain. It is intended that the specification and examples are considered as exemplary only. Other aspects, features and advantages will be apparent upon an examination of the attached drawings and appended claims.

The invention claimed is:

1. A minimal invasive neurosurgery assembly comprising:
   a flush assembly having flush assembly main part with a distal end and a proximal end and with a central passage extending through the main part from the distal end to the proximal end along a longitudinal axis;
   at least one tool insertion assembly including:
      a tool handling part detachably connectable to the flush assembly main part, the tool handling part having a distal end and a proximal end and at least one tool insertion channel that extends from the distal end to the proximal end of the tool handling part; and
      an inner sheath connected to the tool handling part, the inner sheath having an inner sheath wall and at least one lumen extending parallel to the longitudinal axis and in which an associated one of the at least one tool insertion channel emanates, the inner sheath being insertable through the central passage of the flush assembly main part,
   wherein the flush assembly main part includes:
   at least one ring channel that extends circumferentially around the central passage and that is formed by an associated portion of the central passage at an axial position of the central passage that has a diameter that is larger than the diameter of the central passage,
   at least one connecting nipple configured to connect a flushing tube; and
   at least one flush channel extending through the connecting nipple to the associated ring channel and emanating in the ring channel; and wherein the inner sheath includes:
  at least one flush lumen extending parallel to the longitudinal axis; and
  at least one flush passage extending through the inner sheath wall and emanating in an associated one of the at least one flush lumen, the flush passage being positioned at a longitudinal position of the inner sheath that corresponds with the position of an associated one of the at least one ring channel when the tool handling part is connected to the flush assembly main part so that a fluid connection is present between the at least one flush channel extending in the associated connecting nipple and the associated lumen.

2. The neurosurgery assembly according to claim 1, wherein the inner sheath wall has a first position and a second position, the inner sheath wall in the first position having, in cross section, an outer circumference that is convex, and the inner sheath wall in the second position having, in cross section, an outer circumference that includes concave parts so that the total cross sectional area of the inner sheath having its wall in the second position is reduced relative to the total cross sectional area of the inner sheath having its wall in the first position.

3. The neurosurgery assembly according to claim 1, including:
  an outer sheath with a distal end and a proximal end, the outer sheath having an outer sheath wall that bounds an outer sheath channel that extends along a longitudinal axis and that has a distal opening at the distal end and an proximal opening at the proximal end, the flush assembly main part being connected to the outer sheath adjacent the proximal end of the outer sheath and the outer sheath channel being connected to the central passage, the inner sheath being insertable into outer sheath channel.

4. The neurosurgery assembly according to claim 3, wherein the outer sheath wall has a first position and a second position, the outer sheath wall in the first position having, in cross section, an outer circumference that is convex, and the outer sheath wall in the second position having, in cross section, an outer circumference that includes concave parts so that the total cross sectional area of the outer sheath having its wall in the second position is reduced relative to the total cross sectional area of the outer sheath having its wall in the first position.

5. The neurosurgery assembly according to claim 3, including:
  a dummy tool insertion assembly having a tool handling part and a dummy inner sheath of which at least a distal end is closed off, the length of the dummy inner sheath being such that in a mounted condition of the dummy tool insertion assembly on the flush assembly main part, the distal end of the dummy inner sheath also closes off the distal opening of the outer sheath.

6. The neurosurgery assembly according to claim 1, including:
  a fixation assembly configured to connect with a skull of a patient the inner sheath or, alternatively an outer sheath with a distal end and a proximal end, the outer sheath having an outer sheath wall that bounds an outer sheath channel that extends along a longitudinal axis and that has a distal opening at the distal end and an proximal opening at the proximal end, the flush assembly main part being connected to the outer sheath adjacent the proximal end of the outer sheath and the outer sheath channel being connected to the central passage, the inner sheath being insertable into outer sheath channel.

7. The neurosurgery assembly according to claim 6, the fixation assembly including:
  a skull clamp assembly configured to clamp the fixation assembly on the skull; and
  an sheath clamp assembly configured to clamp the outer sheath, or alternatively the inner sheath to the skull clamp assembly in a range of different positions along the longitudinal axis of the outer or inner sheath.

8. The neurosurgery assembly according to claim 6, the fixation assembly including:
  a ring part with a central opening;
  a number of flexible legs each having a proximal end that is connected with the ring part, each leg extending, in a mounted condition substantially parallel to the longitudinal axis and each having a distal end with a protrusion that extends radial outwardly; and
  the legs being positioned relative to each other so that radial inward sides of the legs define a sheath passage of which the diameter is so small that, in a mounted condition of the fixation assembly in a hole in the skull and in a mounted condition of the outer sheath or, alternatively the inner sheath the radial inward sides of the legs engage the outer sheath wall or, alternatively, the inner sheath wall to maintain the sheath in a stable position relative to the fixation assembly.

9. The neurosurgery assembly according to claim 8, wherein the fixation assembly includes:
  a bush having a central passage through which the outer sheath or, alternatively the inner sheath is insertable and having external screw thread that is configured to directly engage the skull material bounding the hole in the skull.

10. The neurosurgery assembly according to claim 7, wherein the skull clamp assembly includes:
  a central part having a number of flexible legs extending, in a mounted condition parallel to the longitudinal axis and each having a distal end with a protrusion that extends radial outwardly, each leg having a proximal end that is integrally connected with a distal end of a central bush that has external screw thread; and
  a fixation bush having internal screw thread configured to co-operate with the external screw thread of the central bush.

11. The neurosurgery assembly according to claim 7, wherein the sheath clamp assembly includes:
  a unitary piece of semi-rigid material including a circumferential part having two diametrically opposed gripping portions on a radial outward peripheral side of the circumferential part and having two diametrically opposed clamping fingers extending radial inwardly from a radial inward side of the circumferential part, the gripping portions being positioned relative to the fingers so that a radial inward movement of the gripping portions effected by pressure exerted thereon causes a radial outward movement of the fingers.

12. The neurosurgery assembly according to claim 1, including:
  a connector to axially fixate the inner sheath relative to an endoscope that is inserted into the at least one lumen of the inner sheath.

13. The neurosurgery assembly according to claim 1, wherein the tool insertion assembly is rotatable relative to the flush assembly around the longitudinal axis.

14. The neurosurgery assembly according to at least claim 13, including:
   a rotation assembly configured to facilitate rotational positioning of the tool insertion assembly relative to the flush assembly.

15. The neurosurgery assembly of claim 1, the tool handling part having at least one tool insertion channel extending from a proximal end to a distal end of the tool handling part and emanating in an associated one of the at least one flush lumen.

16. The neurosurgery assembly according to claim 1, wherein at least one of said tool insertion channels includes a valve.

17. The neurosurgery assembly according to claim 1, wherein the inner sheath includes a first and a second lumen the first lumen having a diameter that differs from the diameter of the second lumen.

18. The neurosurgery assembly according to claim 1, wherein the inner sheath includes a lumen that is bounded by at least one flexible wall part that has at least a stable first position towards it is biased, the lumen being fit for accommodating without play a tool having a first diameter when the at least one flexible wall part is in the stable first position, the lumen being fit for accommodating without substantial play a tool having a second diameter that is different from the first diameter when the at least one flexible wall part is moved out of the first position towards which it is biased.

19. The neurosurgery assembly according to claim 1, including:
   a pressure sensor configured to provide a signal that is indicative of one of fluid pressure and thrust force.

20. The neurosurgery assembly according to claim 1, including:
   an insertion depth indicator that indicates a character that is indicative for the insertion depth of the outer sheath or, alternatively the inner sheath, the insertion depth indicator being configured to be visible from a proximal end of the neurosurgery assembly when looking in the direction of a distal end of the neurosurgery assembly.

21. Kit of parts including a single outer package that contains the neurosurgery assembly according to claim 1 in a sterilized atmosphere.

22. A method for performing a neurosurgery operation on the brain, including:
   providing the neurosurgery assembly according to claim 1;
   determining a region in which the operation has to be performed and based on that determining a position at which a hole has to be drilled in the skull;
   drilling a hole in the skull;
   inserting an inner sheath of the assembly through the hole; and
   inserting at least one of an endoscope and a tool into the tool insertion assembly through an associated tool insertion channel into an associated one of the lumen of the inner sheath.

23. The method of claim 22 including:
   providing the neurosurgery assembly having an outer sheath with a distal end and a proximal end, the outer sheath having an outer sheath wall that bounds an outer sheath channel that extends along a longitudinal axis and that has a distal opening at the distal end and an proximal opening at the proximal end, the flush assembly main part being connected to the outer sheath adjacent the proximal end of the outer sheath and the outer sheath channel being connected to the central passage, the inner sheath being insertable into outer sheath channel;
   providing the neurosurgery assembly having a fixation assembly configured to connect with a skull of a patient the inner sheath or, alternatively an outer sheath with a distal end and a proximal end, the outer sheath having an outer sheath wall that bounds an outer sheath channel that extends along a longitudinal axis and that has a distal opening at the distal end and an proximal opening at the proximal end, the flush assembly main part being connected to the outer sheath adjacent the proximal end of the outer sheath and the outer sheath channel being connected to the central passage, the inner sheath being insertable into outer sheath channel;
   connecting the fixation assembly to the skull of the patient after drilling the hole; and
   connecting the outer sheath to the fixation assembly to keep it stationary relative to the skull.

24. The method of claim 22 including:
   providing the neurosurgery assembly having a fixation assembly configured to connect with a skull of a patient the inner sheath or, alternatively an outer sheath with a distal end and a proximal end, the outer sheath having an outer sheath wall that bounds an outer sheath channel that extends along a longitudinal axis and that has a distal opening at the distal end and an proximal opening at the proximal end, the flush assembly main part being connected to the outer sheath adjacent the proximal end of the outer sheath and the outer sheath channel being connected to the central passage, the inner sheath being insertable into outer sheath channel;
   connecting the fixation assembly to the skull of the patient after drilling the hole; and
   connecting the inner sheath to the fixation assembly to keep it stationary relative to the skull.

25. The method of claim 22 including:
   providing the neurosurgery assembly having an outer sheath with a distal end and a proximal end, the outer sheath having an outer sheath wall that bounds an outer sheath channel that extends along a longitudinal axis and that has a distal opening at the distal end and an proximal opening at the proximal end, the flush assembly main part being connected to the outer sheath adjacent the proximal end of the outer sheath and the outer sheath channel being connected to the central passage, the inner sheath being insertable into outer sheath channel, wherein the outer sheath wall has a first position and a second position, the outer sheath wall in the first position having, in cross section, an outer circumference that is convex, and the outer sheath wall in the second position having, in cross section, an outer circumference that includes concave parts so that the total cross sectional area of the outer sheath having its wall in the second position is reduced relative to the total cross sectional area of the outer sheath having its wall in the first position;
   inserting the outer sheath into the skull when the outer sheath wall is in the second position in which the outer sheath wall has, in cross section, an outer circumference that includes concave parts so that the total cross sectional area of the outer sheath is reduced; and after the inserting
   bringing the outer sheath wall into the first position in which the outer sheath wall has, in cross section, an outer circumference that is convex.

26. The method of claim 22 including:
   providing the neurosurgery assembly having the inner sheath wall with a first position and a second position, the inner sheath wall in the first position having, in cross section, an outer circumference that is convex, and the inner sheath wall in the second position having, in cross section, an outer circumference that includes concave parts so that the total cross sectional area of the inner sheath having its wall in the second position is reduced relative to the total cross sectional area of the inner sheath having its wall in the first position;

inserting the inner sheath into the skull when the inner sheath wall is in the second position in which the inner sheath wall has, in cross section, an outer circumference that includes concave parts so that the total cross sectional area of the inner sheath is reduced; and after the inserting bringing the inner sheath wall into the first position in which the wall has, in cross section, an outer circumference that is convex.

27. The method of claim 22 including:

providing the neurosurgery assembly providing the flush assembly main part including:

at least one ring channel that extends circumferentially around the central passage and that is formed by an associated portion of the central passage at an axial position of the central passage that has a diameter that is larger than the diameter of the central passage, at least one connecting nipple configured to connect a flushing tube; and at least one flush channel extending through the connecting nipple to the associated ring channel and emanating in the ring channel; and the inner sheath including:

at least one flush passage extending through the inner sheath wall and emanating in an associated flush lumen, the flush passage being positioned at a longitudinal position of the inner sheath that corresponds with the position of an associated one of the at least one ring channel when the tool handling part is connected to the flush assembly main part so that a fluid connection is present between the at least one flush channel extending in the associated connecting nipple and the associated lumen;

connecting at least one flushing tube to the at least one connecting nipple;

supplying flushing fluid via the at least one flush channel to the associated ring channel, the at least one flush passage in the inner sheath wall and into the associated flush lumen; and manipulating at least one of an endoscope or a tool inserted into the tool insertion assembly during supplying flushing fluid while keeping the flush assembly main part stationary.

28. The method of claim 22 including:

providing the neurosurgery assembly having the inner sheath including a lumen that is bounded by at least one flexible wall part that has at least a stable first position towards it is biased, the lumen being fit for accommodating without play a tool having a first diameter when the at least one flexible wall part is in the stable first position, the lumen being fit for accommodating without substantial play a tool having a second diameter that is different from the first diameter when the at least one flexible wall part is moved out of the first position towards which it is biased;

inserting the tool having a first diameter into the lumen that is bounded by at least one flexible wall part and that is biased towards a stable first position, the tool having the first diameter being accommodated without play when the at least one flexible wall part is in the stable first position; and inserting the tool having a second diameter that is different from the first diameter in the lumen that is bounded by at least one flexible wall part thereby bringing the flexible wall part out of the first position towards which it is biased so that the tool having the second diameter is accommodated without substantial play in the lumen with the at least one flexible wall part.

29. A minimal invasive neurosurgery assembly comprising:

a flush assembly having flush assembly main part with a distal end and a proximal end and with a central passage extending through the main part from the distal end to the proximal end along a longitudinal axis;

at least one tool insertion assembly including:

a tool handling part detachably connectable to the flush assembly main part, the tool handling part having a distal end and a proximal end and at least one tool insertion channel that extends from the distal end to the proximal end of the tool handling part; and an inner sheath connected to the tool handling part, the inner sheath having an inner sheath wall and at least one lumen extending parallel to the longitudinal axis and in which an associated one of the at least one tool insertion channel emanates, the inner sheath being insertable through the central passage of the flush assembly main part; and a dummy tool insertable into the at least one lumen of the inner sheath, the dummy tool having at least one dummy tool insert of which at least a distal end is closed off, the length of the at least one dummy tool insert being such that in a mounted condition of the dummy tool on tool handling part, the distal end of the at least one dummy tool insert also closes off the distal opening of an associated one of the at least one lumen.

30. A minimal invasive surgery assembly comprising at least one insertion assembly including a sheath extending along a longitudinal axis, the sheath having a sheath wall and at least one lumen extending parallel to the longitudinal axis, the sheath wall having a first position and a second position, the sheath wall in the first position having, in cross section, an outer circumference that is convex, and the sheath wall in the second position having, in cross section, an outer circumference that includes concave parts so that the total cross sectional area of the sheath having its wall in the second position is reduced relative to the total cross sectional area of the sheath having its wall in the first position.

* * * * *